United States Patent [19]
Lee et al.

[11] Patent Number: 6,017,918
[45] Date of Patent: Jan. 25, 2000

[54] PHENYL GLYCINE COMPOUNDS AND METHODS OF TREATING ATHEROSCLEROSIS AND RESTENOSIS

[75] Inventors: Helen Tsenwhei Lee, Ann Arbor, Mich.; Mark Alan Massa, Ballwin, Mo.; William Chester Patt, Chelsea; Bruce David Roth, Plymouth, both of Mich.

[73] Assignee: Warner-Lambert Company, Morris Plains, N.J.

[21] Appl. No.: 09/360,556

[22] Filed: Jul. 26, 1999

Related U.S. Application Data

[60] Provisional application No. 60/095,550, Aug. 6, 1998.

[51] Int. Cl.⁷ .................. A61K 31/215; A61K 31/535; C07D 295/15
[52] U.S. Cl. .................. 514/239.2; 562/445; 562/446; 564/165; 544/171; 544/399; 546/264; 546/312; 546/335; 548/569; 549/77; 549/438; 549/439; 549/494; 558/414; 560/21; 560/39; 560/40
[58] Field of Search .................. 544/171; 560/40; 562/445; 514/239.2

[56] References Cited

U.S. PATENT DOCUMENTS

| | | |
|---|---|---|
| 4,535,165 | 8/1985 | Moore et al. . |
| 5,234,939 | 8/1993 | Capiris et al. . |
| 5,489,611 | 2/1996 | Lee et al. . |
| 5,491,172 | 2/1996 | Lee et al. . |

FOREIGN PATENT DOCUMENTS

| | | |
|---|---|---|
| 617001 | 2/1994 | European Pat. Off. . |
| 95/21151 | 8/1995 | WIPO . |
| 96/08487 | 3/1996 | WIPO . |
| 96/09818 | 4/1996 | WIPO . |
| 97/02037 | 1/1997 | WIPO . |
| 97/02266 | 1/1997 | WIPO . |
| 97/05095 | 2/1997 | WIPO . |

OTHER PUBLICATIONS

Senuma et al, *Chemical Abstracts*, vol. 91, No. 57538, 1979.
Isomura, et a., *Chem. Pharm. Bull.*, "Synthesis and Anti–inflammatory Activity of 2,6–Di–tert–butylphenols with a Heterocyclic Group at the 4–Z Position. III", 1984, vol. 32:1, pp. 152–165.
Lazer, et al., *J. Med. Chem.*, "Antinnflammatory 2,6–Di–tert–butyl–4–(2–arylethenyl)phenos", 1989, vol. 32, pp. 100–104.

*Primary Examiner*—Robert W. Ramsuer
*Attorney, Agent, or Firm*—Charles W. Ashbrook

[57] ABSTRACT

The present invention provides compounds having the Formula I

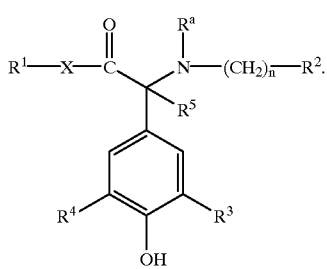

The present invention also provides methods of treating atherosclerosis, coronary heart disease, and restenosis using the compounds of Formula I, and pharmaceutical compositions comprising the compounds of Formula I.

22 Claims, No Drawings

PHENYL GLYCINE COMPOUNDS AND METHODS OF TREATING ATHEROSCLEROSIS AND RESTENOSIS

This application claims the benefit of provisional application No. 60/095,550 filed Aug. 6, 1998.

FIELD OF THE INVENTION

The present invention relates to compounds that are phenyl glycines, and to methods of treating atherosclerosis, coronary heart disease, and restenosis using the phenyl glycine compounds. The invention also relates to a pharmaceutical composition that comprises a phenyl glycine of the present invention.

BACKGROUND OF THE INVENTION

Vascular diseases such as coronary heart disease, atherosclerosis, stroke, restenosis, and peripheral vascular disease, remain the leading cause of death and disability throughout the world. About 1.5 million people die each year in the United States alone from myocardial infarction resulting from congestive heart failure. While diet and life style can accelerate the onset of vascular diseases, genetic predisposition leading to dyslipidemia is a significant factor in vascular-related disabilities and deaths. "Dyslipidemia" means abnormal levels of lipoproteins in blood plasma.

Several risk factors have been associated with increased risk of vascular disease. Among these are the dyslipidemias of high levels of low-density lipoprotein (LDL), and low levels of high-density lipoproteins (HDL). The ratio of HDL- to LDL-cholesterol is often used to assess the risk of vascular disease. A high ratio of HDL/LDL cholesterol is desirable. Compounds that increase this ratio by either lowering LDL or increasing HDL, or both, therefore, are beneficial. Recent studies have also shown that elevated levels of lipoprotein(a), "Lp(a)", are detrimental.

Lp(a) appears to be undesirable, since elevated levels of Lp(a) have been associated with the development of atherosclerosis, coronary heart disease, myocardial infarction, stroke, cerebral infarction, and restenosis following balloon angioplasty. In fact, Lp(a) appears to be an excellent predictor for stroke. Accordingly, high concentrations of Lp(a) is one of the major risk factors leading to death from heart disease.

Lp(a) is composed of LDL and a high molecular weight glycoprotein called apolipoprotein(a), apo(a). Epidemiological studies show that, when present in high levels in the plasma, Lp(a) is an independent risk factor for premature atherosclerotic coronary heart disease. A concentration of 0.30 g/L in plasma is considered to double the risk of premature coronary heart disease and has been used as a clinical set point to determine what plasma concentrations of Lp(a) are considered above normal and for which treatment to lower plasma Lp(a) levels may be desirable.

SUMMARY OF THE INVENTION

The present invention provides compounds having the Formula I

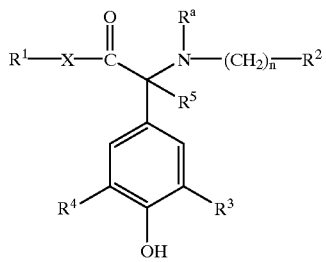

wherein
each $R^1$ is independently hydrogen or $C_1$–$C_6$ alkyl;
$R^2$ is hydrogen, $C_1$–$C_6$ alkyl, heteroaryl, substituted heteroaryl, aryl, substituted aryl, $C_3$–$C_8$ cycloalkyl, or substituted $C_3$–$C_8$ cycloalkyl;
each $R^3$ and $R^4$ is independently $C_1$–$C_6$ alkyl, —$OC_1$–$C_6$ alkyl, or phenyl;
$R^a$ is hydrogen, $C_1$–$C_6$ alkyl, —$(CH_2)_n$-heteroaryl, —$(CH_2)_n$-substituted heteroaryl, —$(CH_2)_n$aryl, —$(CH_2)_n$-substituted aryl, —$(CH_2)_n$—$C_3$–$C_8$ cycloalkyl, —$(CH_2)_n$ substituted $C_3$–$C_8$ cycloalkyl, or $R^a$ and $R^2$ taken together with the N and any —$(CH_2)_n$— form a ring structure comprised of from 4 to 8 atoms and including 1 or 2 heteroatoms;
each n is independently 0, 1, 2, or 3;
$R^5$ is hydrogen or $C_1$–$C_6$ alkyl;

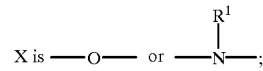

and the pharmaceutically acceptable salts thereof.
In a preferred embodiment, $R^1$ is —$CH_2CH_3$.
In a preferred embodiment, X is —O—.
In another preferred embodiment, $R^a$ is hydrogen.
In a preferred embodiment, $R^3$ and $R^4$ are

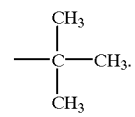

In a preferred embodiment, $R^2$ is pyridyl.
In a preferred embodiment, X is —O—; $R^1$ is —$CH_2CH_3$; $R^a$ is hydrogen; and
$R^3$ and $R^4$ are

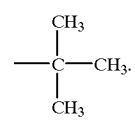

In a more preferred embodiment, $R^2$ is pyridyl, phenyl, substituted phenyl, cyclohexyl, cyclopropyl, furyl, or thienyl.

Also provided are compounds having the Formula I

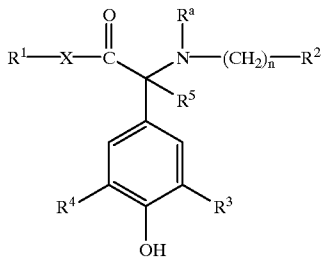

wherein
each $R^1$ is independently hydrogen or ethyl;
$R^2$ is pyridyl, phenyl, substituted phenyl, cyclohexyl, cyclopropyl, furyl, or thienyl;

$R^3$ and $R^4$ are each

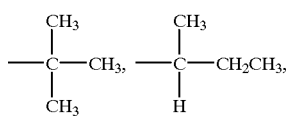

$R^5$ is hydrogen;
$R^a$ is hydrogen, or $C_1$–$C_6$ alkyl;
n is 0 or 1; and
the pharmaceutically acceptable salts thereof.
In a preferred embodiment of Formula I when $R^2$ is substituted phenyl, the substituents are selected from the group —$NH_2$, —$N(CH_3)_2$,

—$OCH_3$, —$OCH_2CH_3$, —F, —Cl, —$NO_2$, —$CF_3$, —CN, —OH, and —$OCH_2CH_2N(CH_2CH_3)_2$.
In a more preferred embodiment, X is —O—;
$R^4$ and $R^3$ are

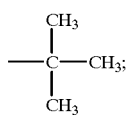

$R^a$ and $R^2$ are —$CH_3$; and
n is O.
In a more preferred embodiment, the present invention provides the compounds:
(3,5-Di-tert-butyl-4-hydroxy-phenyl)-[(pyridin-3-yl)-amino]-acetic acid ethyl ester;
(3,5-Di-tert-butyl-4-hydroxy-phenyl)-[(pyridin-3-ylmethyl)-amino]-acetic acid ethyl ester;
(3,5-Di-tert-butyl-4-hydroxy-phenyl)-[(pyridin-4-ylmethyl)-amino]-acetic acid ethyl ester;
(3,5-Di-tert-butyl-4-hydroxy-phenyl)-[pyridin-2-ylmethyl)-amino]-acetic acid ethyl ester;
Benzylamino-(3,5-di-tert-butyl-4-hydroxy-phenyl)-acetic acid ethyl ester;
(Cyclohexylmethyl-amino)-(3,5-di-tert-butyl-4-hydroxy-phenyl)-acetic acid ethyl ester;
(3,5-Di-tert-butyl-4-hydroxy-phenyl)-[(pyridin-3-ylmethyl)-amino]-acetic acid;
(3,5-Di-tert-butyl-4-hydroxy-phenyl)-[(cyclohexyl)-amino]-acetic acid ethyl ester;
(Bis-pyridin-3-ylmethyl-amino)-(3,5-di-tert-butyl-4-hydroxy-phenyl)-acetic acid ethyl ester;
(3-Chloro-benzylamino)-(3,5-di-tert-butyl-4-hydroxy-phenyl)-acetic acid ethyl ester;
(Cyclohexylmethyl-amino)-(2'-hydroxy-[1,1';3',1"]terphenyl-5'-yl)-acetic acid ethyl ester;
(Cyclopropylmethyl-amino)-(3,5-di-tert-butyl-4-hydroxy-phenyl)-acetic acid ethyl ester;
(Cyclohexylmethyl-amino)-(3,5-di-sec-butyl-4-hydroxy-phenyl)-acetic acid ethyl ester;
(3,5-Di-tert-butyl-4-hydroxy-phenyl)-(3-hydroxy-4,5-dimethoxy-benzylamino)-acetic acid ethyl ester;
(3,5-Di-tert-butyl-4-hydroxy-phenyl)-(3,4,5-trimethoxy-benzylamino)-acetic acid ethyl ester;
(Cyclohexylmethyl-pyridin-3-ylmethyl-amino)-(3,5-di-tert-butyl-4-hydroxy-phenyl)-acetic acid ethyl ester;
(3,5-Di-tert-butyl-4-hydroxy-phenyl)-dimethylamino-acetic acid ethyl ester;
(3,5-Di-tert-butyl-4-hydroxy-phenyl)-[(3,5-Di-tert-butyl-4-hydroxy-phenyl)methyl)-amino]-acetic acid ethyl ester;
(3,5-Di-tert-butyl-4-hydroxy-phenyl)-[methyl-(4-methyl-benzyl)-amino]-acetic acid ethyl ester;
(3,5-Di-tert-butyl-4-hydroxy-phenyl)-[(7-methoxy-benzo[1,3]dioxol-5-ylmethyl)-amino]-acetic acid ethyl ester;
(3,5-Di-tert-butyl-4-hydroxy-phenyl)-(3,4-dimethoxy-benzylamino)-acetic acid ethyl ester;
(Cyclohexylmethyl-amino)-(3,5-di-tert-butyl-4-hydroxy-phenyl)-acetic acid;
N-Benzyl-2-(cyclohexylmethyl-amino)-2-(3,5-di-tert-butyl-4-hydroxy-phenyl)-acetamide;
(3,5-Di-tert-butyl-4-hydroxy-phenyl)-[(pyridin-3-ylmethyl)-amino]-acetic acid isopropyl ester;
(3,5-Di-tert-butyl-4-hydroxy-phenyl)-[(thiophen-2-ylmethyl)-amino]-acetic acid ethyl ester;
2-(Cyclohexylmethyl-amino)-2-(3,5-di-tert-butyl-4-hydroxy-phenyl)-N-ethyl-acetamide;
(3,5-Di-tert-butyl-4-hydroxy-phenyl)-[(2-phenyl-phenylmethyl)-amino]-acetic acid ethyl ester;
(3,5-Di-tert-butyl-4-hydroxy-phenyl)-phenethylamino-acetic acid ethyl ester;
(3,5-Di-tert-butyl-4-hydroxy-phenyl)-[(butyl)-amino]-acetic acid ethyl ester;
(4-Amino-benzylamino)-(3,5-di-tert-butyl-4-hydroxy-phenyl)-acetic acid ethyl ester;
[(6-Amino-benzo[1,3]dioxol-5-ylmethyl)-amino]-(3,5-di-tert-butyl-4-hydroxy-phenyl)-acetic acid ethyl ester;
(3,5-Di-tert-butyl-4-hydroxy-phenyl)-(4-methoxy-benzylamino)-acetic acid ethyl ester;
(2-Chloro-benzylamino)-(3,5-di-tert-butyl-4-hydroxy-phenyl)-acetic acid ethyl ester;
(4-Cyano-benzylamino)-(3,5-di-tert-butyl-4-hydroxy-phenyl)-acetic acid ethyl ester;
(3,5-Di-tert-butyl-4-hydroxy-phenyl)-(3,5-dichloro-2-hydroxy-benzylamino)-acetic acid ethyl ester;
(3,5-Di-tert-butyl-4-hydroxy-phenyl)-(2,4-dichloro-benzylamino)-acetic acid ethyl ester;
(3,5-Di-tert-butyl-4-hydroxy-phenyl)-[4-(2-diethylamino-ethoxy)-benzylamino]-acetic acid ethyl ester;

(3,5-Di-tert-butyl-4-hydroxy-phenyl)-[4-dimethylamino-benzylamino]-acetic acid ethyl ester;
(3,5-Di-tert-butyl-4-hydroxy-phenyl)-(3-ethoxy-4-hydroxy-benzylamino)-acetic acid ethyl ester;
(3,5-Di-tert-butyl-4-hydroxy-phenyl)-(2-fluoro-benzylamino]-acetic acid ethyl ester;
(3,5-Di-tert-butyl-4-hydroxy-phenyl)-[(furan-3-ylmethyl)-amino]-acetic acid ethyl ester;
(3,5-Di-tert-butyl-4-hydroxy-phenyl)-(3-hydroxy-benzylamino)-acetic acid ethyl ester;
(3,5-Di-tert-butyl-4-hydroxy-phenyl)-(4-hydroxy-benzylamino)-acetic acid ethyl ester;
(3,5-Di-tert-butyl-4-hydroxy-phenyl)-(2-methoxy-benzylamino)-acetic acid ethyl ester;
(3,5-Di-tert-butyl-4-hydroxy-phenyl)-(4-nitro-benzylamino)-acetic acid ethyl ester;
(3,5-Di-tert-butyl-4-hydroxy-phenyl)-[(thiophen-3-ylmethyl)-amino]-acetic acid ethyl ester;
(3,5-Di-tert-butyl-4-hydroxy-phenyl)-(2-trifluoromethyl-benzylamino)-acetic acid ethyl ester;
(3,5-Di-tert-butyl-4-hydroxy-phenyl)-(3-trifluoromethyl-benzylamino)-acetic acid ethyl ester;
(3,5-Di-tert-butyl-4-hydroxy-phenyl)-(4-hydroxy-3-methoxy-benzylamino)-acetic acid ethyl ester;
(3,5-Di-tert-butyl-4-hydroxy-phenyl)-(3-nitro-benzylamino)-acetic acid ethyl ester;
(3,5-Di-tert-butyl-4-hydroxy-phenyl)-(ethylamino)-acetic acid ethyl ester;
(3,5-Di-tert-butyl-4-hydroxy-phenyl)-(N-pyrollidinyl)-acetic acid ethyl ester;
(3,5-Di-tert-butyl-4-hydroxy-phenyl)-dimethylamino-acetic acid t-butyl ester;
(3,5-Di-tert-butyl-4-hydroxy-phenyl)-(N-morpholinyl)-acetic acid ethyl ester;
(3,5-Di-tert-butyl-4-hydroxy-phenyl)-[(N'-methyl)-N-piperazinyl]-acetic acid ethyl ester;
Diethyl-(3,5-Di-tert-butyl-4-hydroxy-phenyl)-(N-morpholinyl)-acetamide; and
(3,5-Di-tert-butyl-4-hydroxy-phenyl)-dimethylamino-acetic acid, 2-phenylethyl ester.

Also provided is a method of lowering plasma Lp(a) in a patient, the method comprising administering to a patient in need of Lp(a) lowering a therapeutically effective amount of a compound of Formula I.

Also provided is a method of treating atherosclerosis, the method comprising administering to a patient having atherosclerosis a therapeutically effective amount of a compound of Formula I.

Also provided is a method of treating coronary heart disease, the method of comprising administering to a patient having coronary heart disease a therapeutically effective amount of a compound of Formula I.

Also provided is a method of treating or preventing restenosis, the method comprising administering to a patient having restenosis at risk of having restenosis a therapeutically effective amount of a compound of Formula I.

Also provided is a pharmaceutical composition that comprises a compound of Formula I.

DETAILED DESCRIPTION OF THE INVENTION

The term "alkyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like. The alkyl group can also be substituted with one or more of the substituents listed below for aryl.

The term "aryl" means an aromatic ring such as phenyl, 5-fluorenyl, 1-naphthyl, or 2-naphthyl group, unsubstituted or substituted by 1 to 3 substituents selected from $C_1$–$C_6$ alkyl, O—$C_1$–$C_6$ alkyl and S—$C_1$–$C_6$ alkyl, —OH, —SH, F, —CN, Cl, Br, I, —$CF_3$, —$NO_2$, —$CO_2H$, —$CO_2C_1$–$C_6$ alkyl,

—$NH_2$, —$NHC_1$—$C_6$ alkyl, or —$N(C_1$–$C_6$alkyl$)_2$, —$O(CO_2)_m N(C_1$–$C_6$ alkyl$)_2$, where m is 0 to 6.

The term "heteroaryl" means an aromatic ring containing one or more heteroatoms. Examples of heteroaryl radicals include thienyl, furyl, pyrrolyl, thiazoyl, pyridyl, imidazolyl, or indolyl group, substituted or unsubstituted by 1 or 2 substituents from the group of substituents described above for aryl. Examples of heteroatoms include nitrogen, oxygen, sulfur, and phosphorus.

The term "cycloalkyl" means a saturated hydrocarbon ring which contains from 3 to 7 carbon atoms, and includes for example, cyclopropyl, cyclobutyl, cyclopentyl, cyclohexyl, adamantyl, and the like. The cycloalkyl group can be substituted with from 1 to 3 substituents from the group of substituents described above for aryl.

The symbol "—" means a bond.

The term "patient" means all animals including humans. Examples of patients include humans, cows, dogs, cats, goats, sheep, and pigs.

A "therapeutically effective amount" is an amount of a compound of the present invention that when administered to a patient ameliorates a symptom of atherosclerosis, coronary heart disease, or restenosis or lowers plasma levels of Lp(a). A therapeutically effective amount of a compound of the present invention can be easily determined by one skilled in the art by administering a quantity of a compound to a patient and observing the result. In addition, those skilled in the art are familiar with identifying patients having restenosis, coronary heart disease, or atherosclerosis or who are at risk of having restenosis, coronary heart disease, or atherosclerosis.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977;66:1–19 which is incorporated herein by reference).

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

The compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The compounds of the present invention can be administered to a patient at dosage levels in the range of about 0.1 to about 2,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depended on a numbers of factors including the requirements of the patient, the severity of the condition being treated, and the pharmacological activity of the compound being used. The determination of optimum dosages for a particular patient is well known to those skilled in the art.

The compounds of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can be synthesized using standard organic methodology, including combinatorial chemistry or by biological processes such as through metabolism. It is intended that the present invention include compounds made by any process.

The compounds of the present invention can be synthesized generally as follows:

With regard to Scheme 1, a phenol is reacted in an organic solvent such as dichloromethane with ethyl oxalyl chloride and a Lewis acid such as aluminum chloride. This gives the phenyloxalyl ester, which is then reacted either with an amine in the presence of a reducing agent such as sodium triacetoxy borohydride to give a compound of the invention. Alternatively, in a two step process, the amine is reacted with the phenyloxalyl derivative in the presence of a dehydrating agent to give the imine derivative as an intermediate. This imine is then reacted with the reducing agent to give a compound of the invention.

With regard to Scheme 2, the phenyloxalyl derivative from Scheme 1 is reacted in an alcoholic solvent with phenyl hydrazine to give the hydrazone. The hydrazone is the reacted with a reducing agent such as zinc dust in acetic acid or catalytically hydrogenated to give the amino ester. The amine is reacted with an aldehyde in an organic solvent such as 1,2-dichloroethane in the presence of a reducing agent such as sodium triacetoxy borohydride. This gives a compound of the invention.

With regard to Scheme 3, a phenol with a p-methyl group is reacted with a brominating agent such as N-bromosuccinimide (NBS) in carbon tetrachloride to give the alpha bromo derivative. This bromide is then reacted with potassium cyanide in an organic solvent such as ethanol or dimethylformamide (DMF) to give the nitrile. The nitrile is then hydrolyzed to the acid with a base such as hydroxide in water. The acid was converted to the ester by reacting the acid with excess alcohol and anhydrous hydrochloric acid. The ester is then reacted with NBS in an organic solvent such as carbon tetrachloride to give the alpha bromo ester. This bromide is then treated with a primary or secondary amine in the presence of an acid scavenger such as triethyl amine in an organic solvent such as tetrahydrofuran (THF) to give a compound of the invention.

With regard to Scheme 4, the final compounds in Schemes 1–3 could then be further reacted with an aldehyde in the presence of a reducing agent such as sodium triacetoxy borohydride in an organic solvent such as 1,2-dichloroethane to give a di-substituted amine of the invention.

SCHEME 1

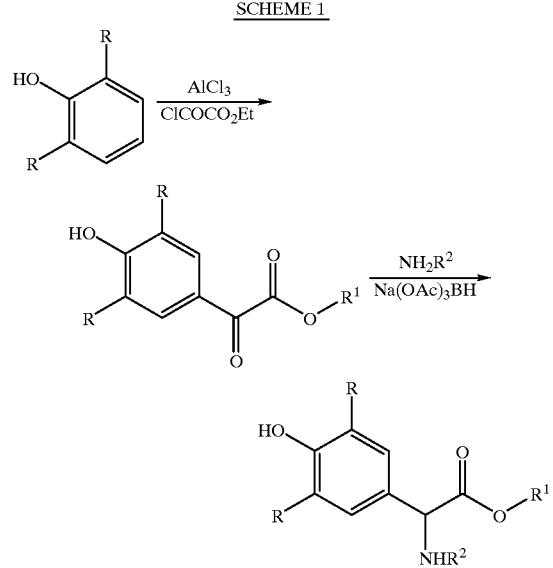

SCHEME 2

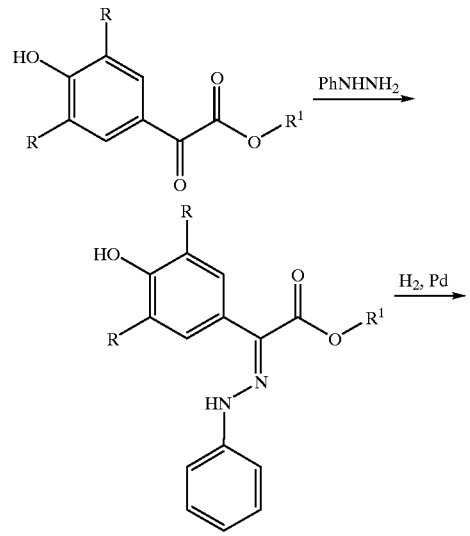

-continued

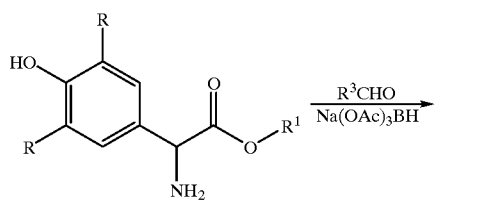

SCHEME 3

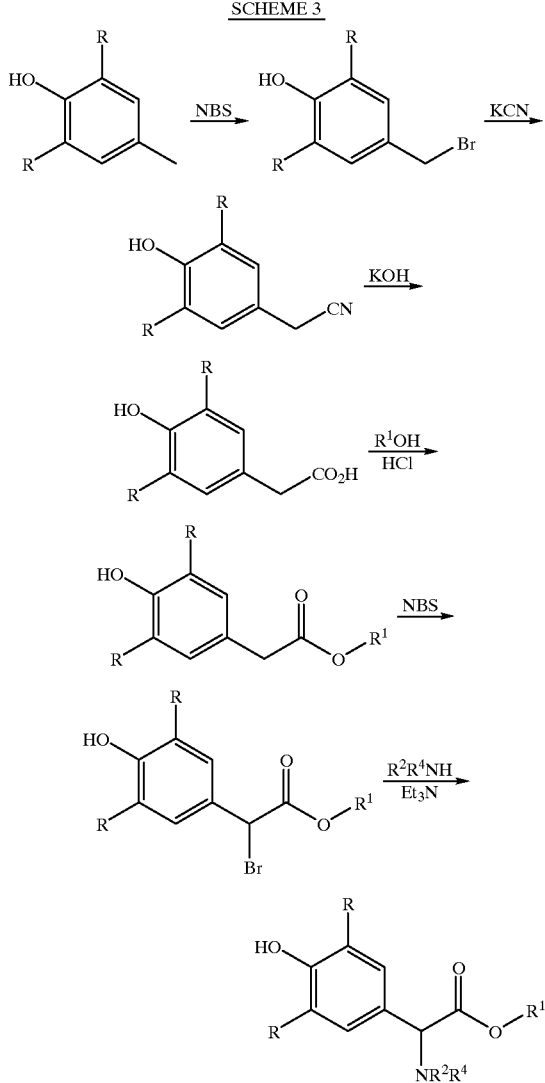

SCHEME 4

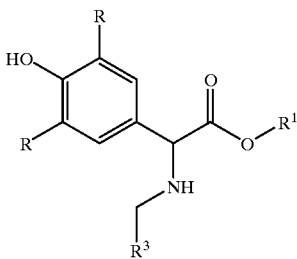

SCHEME 5

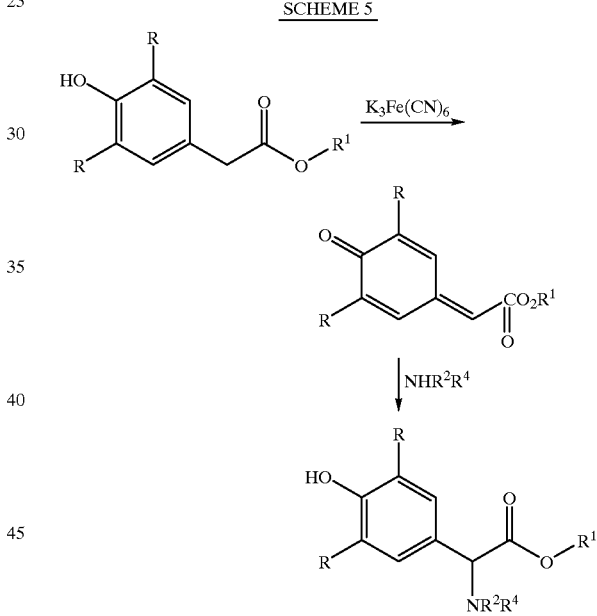

With regard to Scheme 5, the acetate from Scheme 3 (prior to NBS reaction) is reacted with potassium ferricyanate $(K_3Fe(CN)_6)$ in a mixture of benzene and water to give a quinone methine. This is then reacted with an amine in an organic solvent such as THF to give a compound of the invention.

The examples presented below are intended to illustrate particular embodiments of the invention, and are not intended to limit the scope of the specification or the claims in any way.

EXAMPLES

Intermediates

Intermediate 1: Ethyl (3,5-di-t-butyl-4-hydroxyphenyl)-2-oxo-acetate

To a 0° C. mixture of aluminum chloride (24.6 g, 180 mmol) and ethyl oxalyl chloride (24.6 g, 180 mmol) in methylene chloride (350 mL) was added, dropwise over 10 minutes, a solution of 2,6-di-t-butyl phenol (30.9 g, 150 mmol) in methylene chloride (125 mL). The mixture was stirred cold for 1 hour and then warmed to ambient temperature, and stirring was continued for an additional hour. The solution was recooled to 0° C. and carefully quenched with water (300 mL). The organic phase was separated, washed with 1N HCl (300 mL) and then brine (300 mL). The organic phase was dried over magnesium sulfate and evaporated in vacuo to give an olive colored oil, 44.6 g (96%).

MS: $M^+=264$.

Intermediate 2: Ethyl (3,5-di-t-butyl-4-hydroxyphenyl)-2-oxo-acetate, phenyl hydrazone In ethanol (150 mL) was dissolved Intermediate 1 (44.5 g, 146 mmol) and phenyl hydrazine (20.5 g, 190 mmol). The mixture was warmed to reflux and stirred for 24 hours. The solution was cooled to room temperature, to form a precipitate. The solid was collected by filtration and washed with cold ethanol (2×50 mL). The solid was dried at 65° C. in vacuo for 3 hours, 41.5 g (72%).

MS: $M^+=396$.

Intermediate 3: Ethyl (3,5-di-t-butyl-4-hydroxy)-phenyl glycinate

Intermediate 2 (19.6 g, 49.4 mmol) was dissolved in a mixture of ethanol (100 mL) and THF (150 mL) and treated with 1.0 g of 10% Pd/C. This mixture was placed in a hydrogen atmosphere and stirred at 25° C. for 24 hours (at 4 hours and 10 hours an additional 1.0 g of Pd/C was added). The catalyst was filtered from the mixture and the filtrate evaporated in vacuo to give a solid. The solid was recrystallized from hexane (175 mL) to give a white solid, 12.7 g (84%).

MS: $M^+=307$.

Intermediate 4: Ethyl (3,5-diphenyl-4-hydroxyphenyl)-2-oxo-acetate

Synthesized as in Intermediate 1 from 2,6-diphenyl phenol (10.0 g, 40 mmol) and ethyl oxalyl chloride (6.8 g, 50 mmol). This gave 12.5 g (90%) of product.

MS: $M^+=346$.

Intermediate 5: Ethyl (3,5-diphenyl-4-hydroxyphenyl)-2-oxo-acetate, phenyl hydrazone Synthesized as in Intermediate 2 from intermediate 4 (12.0 g, 34.6 mmol) and phenyl hydrazine (4.76 g, 44 mmol). This gave 8.3 g (55%) of product. MS:$M^+=436$.

Intermediate 6: Ethyl (3,5-diphenyl-4-hydroxy)-phenyl glycinate

Formic acid was stirred in zinc dust (9.8 g, 150 mmol) and the solution warmed to 60° C. This was treated in parts with Intermediate 5 (7.5 g, 17.2 mmol). The solution was stirred for an additional 1.5 hours and then cooled to room temperature. The solution was filtered free of zinc solids, and the filtrate was evaporated in vacuo to give a sludge. This was partitioned between saturated sodium bicarbonate (150 mL) and ethyl acetate (200 mL). The organic phase was separated, washed with brine, and dried over magnesium sulfate. The solvents were evaporated in vacuo to give an oil. The oil was purified by chromatography (200 g silica gel, 1:1 [ethyl acetate:methylene chloride]). The appropriate fractions were combined and evaporated in vacuo to give 1.1 g (18%) of product.

MS: $M^+=348$.

Intermediate 7: Ethyl (3,5-di-s-butyl-4-hydroxyphenyl)-2-oxo-acetate

Synthesized as in Intermediate 1 from 2,6-di-s-butyl phenol (10.3 g, 50 mmol) and ethyl oxalyl chloride (8.19 g, 60 mmol). This gave 4.61 g (30%) of product.

MS: $M^+=306$.

Intermediate 8: Ethyl (3,5-di-s-butyl-4-hydroxyphenyl)-2-oxo-acetate, phenyl hydrazone Synthesized as in Intermediate 2 from Intermediate 7 (4.58 g, 15.0 mmol) and phenyl hydrazine (2.16 g, 20 mmol). This gave 3.5 g (59%) of product.

MS: $M^+=396$.

Intermediate 9: Ethyl (3,5-di-s-butyl-4-hydroxy)-phenyl glycinate

Synthesized as in Example 6 from Intermediate 8 (3.3 g, 8.3 mmol). This gave 1.1 g (44%) of product.

Intermediate 10: Ethyl (3,5-di-t-butyl-4-hydroxyphenyl)-acetate

In ethanol (60 mL) was dissolved 3,5-di-t-butyl-4-hydroxyphenyl-acetic acid (8.0 g, 30.3 mmol). The solution was saturated with HCl gas and stirred at room temperature for 18 hours. The mixture was evaporated in vacuo and the residue was dissolved in ethyl acetate (100 mL). The organic phase was washed with water (100 mL) and then brine (100 mL). The organic phase was dried over magnesium sulfate and evaporated in vacuo to give 7.95 g (90%) of the product as an oil.

MS: $M^+=292$.

Intermediate 11: Ethyl 2-bromo-(3,5-di-t-butyl-4-hydroxyphenyl)-acetate

In carbon tetrachloride (15 mL) was dissolved Intermediate 10 (1.46 g, 5.0 mmol) and NBS (1.33 g, 7.5 mmol). The solution was treated with benzoyl peroxide (~2 mg) and warmed to 60° C. and stirred for 18 hours. The mixture was cooled to room temperature and filtered free of insolubles. The filtrate was evaporated in vacuo to give 2.0 g (>100%) of the crude product as an oil.

MS=$M^+=335$.

Intermediate 12: N-BOC-Ethyl (3,5-di-t-butyl-4-hydroxy)-phenyl glycinate

To a solution of Intermediate 3 (1.00 g, 3.25 mmol) in dioxane (10 mL) and water (10 mL) was added $(BOC)_2O$ (0.79 mmol). The mixture stirred for 30 minutes. The resultant cloudy solution was treated with methanol (~2 mL) to clarify and then evaporated. The residue was partitioned between ethyl acetate (50 mL) and water (50 mL). The organic phase was separated, washed with brine, and dried over magnesium sulfate. The solvents were evaporated in vacuo to give 1.26 g (95%) of the solid product. (BOC is tertiary butyloxycarbonyl).

MS: $M^+=406$.

Intermediate 13: N-BOC-(3,5-di-t-butyl-4-hydroxy)-phenyl glycine

To Intermediate 12 (1.26 g, 3.09 mmol) in dioxane (10 mL) was added 1N NaOH (10 mL). The mixture was warmed to reflux for 4 hours and then cooled to room temperature. The mixture was evaporated in vacuo and then dissolved in water (50 mL). This was washed with ether (2×30 mL) and the ether discarded. The aqueous phase was treated with 1N HCl (10 mL) and then extracted with fresh ether (50 mL). The ether was dried over magnesium sulfate and evaporated in vacuo to give the acid as a foam.

MS: $M^+=380$.

Intermediate 14: N-BOC-i-Propyl-(3,5-di-t-butyl-4-hydroxy)-phenyl glycinate

To a solution of Intermediate 13 (1.0 g, 2.65 mmol) in acetone was added isopropyl iodide (284 μL, 2.84 mmol) and potassium carbonate (0.72 g, 5.2 mmol). The mixture vigorously stirred for 1 hour at room temperature then warmed to reflux and stirred 96 hours. The mixture was then filtered and evaporated. The residue was partitioned between ether (50 mL) and water (50 mL). The organic phase was separated and dried over magnesium sulfate. The solvents were evaporated in vacuo to give 0.9 g (80%) of product as a foam.

MS: M+=422.

Intermediate 15: i-Propyl-(3,5-di-t-butyl-4-hydroxy)-phenyl glycinate

A solution of Intermediate 14 (0.9 g, 2.13 mmol) in methylene chloride (20 mL) was saturated with HCl gas and stirred at room temperature for 18 hours. The solution was washed with saturated sodium bicarbonate (20 mL) and dried over magnesium sulfate. The solvents were evaporated in vacuo to give 0.46 g (68%) of the product as a solid.

MS: M+=322.

Intermediate 16: Ethyl (3,5-di-t-butyl-4-hydroxyphenyl)-2-(3-iminopyridyl)-acetate A solution of Intermediate 1 (6.12 g, 20 mmol) and 2-aminopyridine (1.88 g, 20 mmol) in toluene (50 mL) was treated with catalytic p-toluenesulfonic acid. The solution was warmed to reflux for 2 days with Dean-Stark trap removal of water. The solution was treated with molecular sieves and reflux continued for an additional 2 days. The mixture was cooled and evaporated. The residue purified by chromatography (silica gel, 4:1 [(hexane:methylene chloride)]) to give 0.7 g (9%) of the imine.

Intermediate 17: Ethyl (3,5-di-t-butyl-4-oxocyclohexa-2,5-dienylidene)acetate

In benzene (150 mL) was dissolved Intermediate 10 (6.7 g, 22.9 mmol) and this treated with a solution of potassium hydroxide (13.9 g [85%], 210 mmol) and potasium ferricyanide ($K_3Fe(CN)_6$) (15.2 g, 46 mmol) in water (150 mL). The mixture stirred under nitrogen atmosphere at 40° C. for 2 hours. The benzene layer then separated, washed with brine (100 mL) and dried over magnesium sulfate. The solvent was evaporated in vacuo to give a red oil, 6.1 g (92%), which was used as is.

Intermediate 18: 3,5-di-tert-butyl-4-hydroxy-phenyl acetic acid t-butyl ester

The t-butyl ester was obtained by high pressure hydrogenolysis from a solution of 3,5-di-tert-butyl-4-hydroxy-phenyl acetic acid (9.97 g, 37.7 mmol) in dioxane (100 mL), $H_2SO_4$ (1 mL) and isobutylene (100 mL). The product, a pale yellow oil, was obtained in 32% yield.

Intermediate 19: (3,5-di-tert-butyl-4-hydroxy-phenyl)-bromo-acetic acid t-butyl ester To a solution of Intermediate 18 (1.0314 g, 3.22 mmol) in 7.3 mL $CCl_4$ was added N-bromosuccinimide (0.5827 g) and a catalytic amount of benzoyl peroxide. The reaction was heated to 60° C. overnight. The solvent was removed in vacuo. The residue was taken up in ethyl acetate, washed with water and brine, dried over $MgSO_4$, and concentrated to an orange oil (0.8654 g, 2.17 mmol), which was used in the next step without further purification.

Intermediate 20: Diethyl-3,5-di-tert-butyl-4-hydroxy-phenyl acetamide

A solution of 3,5-di-tert-butyl-4-hydroxy-phenyl acetic acid (2.64 g, 10 mmol), HOBT (1.35 g, 10 mmol), DCC (2.06 g, 10 mmol), and diethyl amine (0.81 g, 11 mmol) in methylene chloride was stirred at room temperature for 24 hours. The mixture filtered free of precipitated solid and the filtrate was washed with water (100 mL) and then brine (100 mL). The organic phase was dried over magnesium sulfate and evaporated in vacuo to give a solid. The solid was purified by chromatography (250 g flash silica gel, 5% methanol in methylene chloride) to give 2.15 g (67%) of pure amide.

Intermediate 21: Diethyl (3,5-di-t-butyl-4-oxocyclohexa-2,5-dienylidene)acetamide The compound was synthesized as in Intermediate 17 from Intermediate 20 (1.85 g, 5.8 mmol) and potassium ferricyanide (4.9 g, 11.6 mmol). This gave 1.84 g (100%) of the crude intermediate which was used as is.

Intermediate 22: 3,5-di-tert-butyl-4-hydroxy-phenyl acetic acid 2-phenylethyl ester To a solution of 3,5-di-tert-butyl-4-hydroxy-phenyl acetic acid (2.64 g, 10 mmol) in methylene chloride (25 mL) was added 2-phenylethanol (1.34 g, 11 mmol), DCC (2.1 g, 10.1 mmol), and DMAP (122 mg, 1.0 mmol). The mixture was stirred overnight at room temperature. The mixture filtered free of insolubles and the filtrate was washed with water (50 mL) and then brine (50 mL). The organic phase was dried over magnesium sulfate and evaporated in vacuo to give the crude ester. The intermediate was purified by chromatography (200 g flash silica gel, 85:15, hexane:ethyl acetate) to give 2.89 g (79%) of pure ester. Intermediate 23: (3,5-di-t-butyl-4-oxocyclohexa-2,5-dienylidene)-acetic acid, 2-phenylethyl ester The compound was synthesized as in Intermediate 17 from Intermediate 22 (2.8 g, 7.6 mmol) and potassium ferricyanide (6.42 g, 15.2 mmol). This gave 2.69 g (97%) of crude intermediate which was used as is.

Example 1

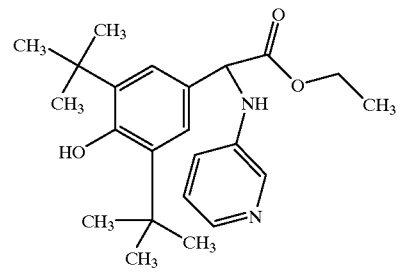

(3,5-Di-tert-butyl-4-hydroxy-phenyl)-[(pyridin-3-yl)-amino]-acetic acid ethyl ester Intermediate 16 (570 mg, 1.49 mmol) was dissolved in ethanol (75 mL) and treated with Raney Nickel (0.5 g). The mixture was stirred in a hydrogen atmosphere at ambient temperature for 21 hours. The mixture was filtered free of catalyst and evaporated in vacuo to give an oil. The compound was purified by chromatography (125 g flash silica gel, 5% methanol/methylene chloride). The appropriate fractions were evaporated in vacuo to give 0.36 g (69%) of the product as a white solid.

MS: M+=385. CHN: calc'd: C, 71.84; H, 8.39; N, 7.29. Found: C, 71.78; H, 8.27; N, 7.29.

Example 2

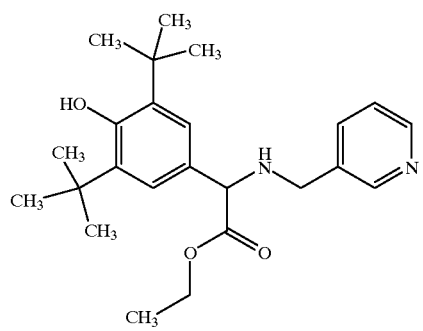

(3,5-Di-tert-butyl-4-hydroxy-phenyl)-[(pyridin-3-ylmethyl)-amino]-acetic acid ethyl ester To a solution of Intermediate 3 (520 mg, 1.69 mmol) and 3-pyridine carboxaldehyde (170 μL, 1.80 mmol) in 1,2-dichloroethane was added sodium triacetoxy borohydride (500 mg, 2.37 mmol). The solution stirred 18 hours at room temperature. This was poured into water and extracted with methylene chloride (50 mL). The organic phase dried over magnesium sulfate and evaporated in vacuo to give an oil. The oil was purified by medium pressure liquid chromatography (MPLC) (125 g silica gel, 10% methanol/methylene chloride). The appropriate fractions were combined and evaporated in vacuo to give a white solid. The solid was triturated with hexane and filtered to collect the solid. This was dried at 60° C. to give 0.45 g (67%) of the compound.

MS: $M^+$=399. CHN: calc'd: C, 72.33; H, 8.60; N, 7.03. Found: C, 72.39; H, 8.50; N, 6.83.

Example 3

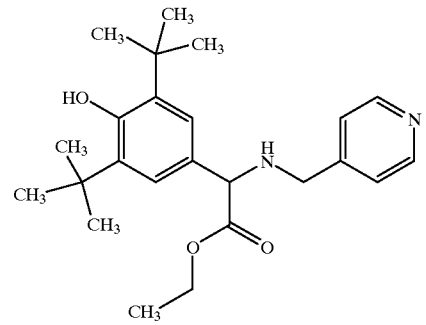

(3,5-Di-tert-butyl-4-hydroxy-phenyl)-[(pyridin-4-ylmethyl)-amino]-acetic acid ethyl ester Synthesized as in Example 2 from Intermediate 3 (490 mg, 1.60 mmol) and 4-pyridine carboxaldehyde (160 μL, 1.68 mmol). This gave 0.29 g (45%) of product.

MS: $M^+$=399. CHN: calc'd: C, 72.33; H, 8.60; N, 7.03. Found: C, 72.43; H, 8.60; N, 6.95.

Example 4

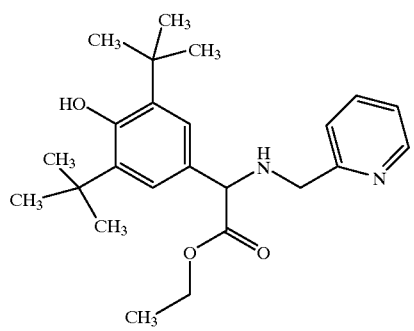

(3,5-Di-tert-butyl-4-hydroxy-phenyl)-[pyridin-2-ylmethyl)-amino]-acetic acid ethyl ester Synthesized as in Example 2 from Intermediate 3 (500 mg, 1.63 mmol) and 2-pyridine carboxaldehyde (164 μL, 1.73 mmol). This gave 0.26 g (40%) of product.

MS: $M^+$=399. CHN: calc'd: C, 72.33; H, 8.60; N, 7.03. Found: C, 72.50; H, 8.66; N, 6.92.

Example 5

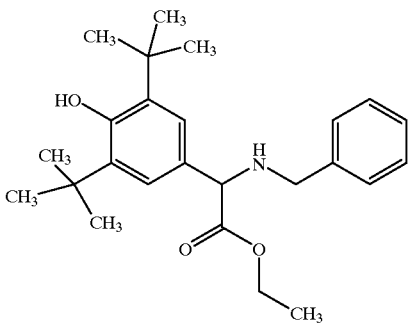

Benzylamino-(3,5-di-tert-butyl-4-hydroxy-phenyl)-acetic acid ethyl ester

Synthesized as in Example 2 from Intermediate 3 (500 mg, 1.63 mmol) and benzaldehyde (176 μL, 1.73 mmol). This gave 0.35 g (54%) of product.

MS: $M^+$=398. CHN: calc'd: C, 75.53; H, 8.87; N, 3.52. Found: C, 75.28; H, 8.89; N, 3.47.

Example 6

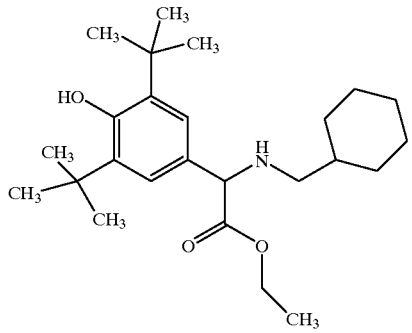

(Cyclohexylmethyl-amino)-(3,5-di-tert-butyl-4-hydroxy-phenyl)-acetic acid ethyl ester Synthesized as in Example 2 from Intermediate 3 (500 mg, 1.63 mmol) and cyclohexyl carboxaldehyde (210 μL, 1.73 mmol). This gave 0.34 g (52%) of product.

MS: M+=404. CHN: calc'd: C, 74.40; H, 10.24; N, 3.47. Found: C, 74.42; H, 10.44; N, 3.39.

Example 7

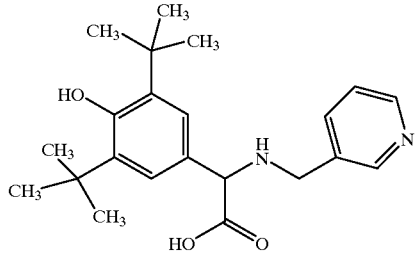

(3,5-Di-tert-butyl-4-hydroxy-phenyl)-[(pyridin-3-ylmethyl)-amino]-acetic acid

A solution of Example 2 (300 mg, 0.75 mmol) in dioxane (10 mL) was treated with 1N NaOH (10 mL) and stirred at room temperature for 4 hours. The mixture was evaporated in vacuo and the residue dissolved in water (30 mL). This was washed with methylene chloride (50 mL) and ethyl acetate (50 mL). The aqueous phase was treated with 1N HCl (10 mL) and extracted with fresh methylene chloride (75 mL) and ethyl acetate (75 mL). These organics were combined and evaporated to give an oil. The oil was dissolved in methylene chloride/hexane and allowed to crystallize. The solid was collected and dried in vacuo to give 0.129 g (46%) of product.

MS: M+=371. CHN: calc'd (for 0.7 HCl salt): C, 66.73; H, 7.81; N, 7.07. Found: C, 67.06; H, 7.77; N, 7.34.

Example 8

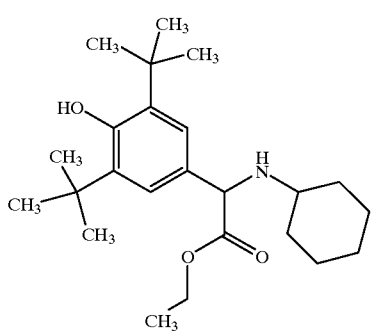

(3,5-Di-tert-butyl-4-hydroxy-phenyl)-[(cyclohexyl)-amino]-acetic acid etyl ester Synthesized as in Example 2, in the presence of acetic acid (100 μL), from Intermediate 3 (500 mg, 1.63 mmol) and cyclohexanone (179 μL, 1.73 mmol). This gave 0.38 g (60%) of product.

MS: M+=390. CHN: calc'd: C, 73.79; H, 10.05; N, 3.50. Found: C, 73.99; H, 10.09; N, 3.60.

Example 9

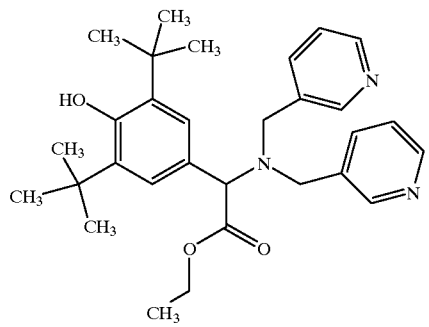

(Bis-pyridin-3-ylmethyl-amino)-(3,5-di-tert-butyl-4-hydroxy-phenyl)-acetic acid ethyl ester Synthesized as in Example 2, in the presence of acetic acid (280 μL), from Intermediate 3 (500 mg, 1.63 mmol) and 3-pyridine carboxaldehyde (462 μL, 4.90 mmol). This gave 0.36 g (45%) of product.

MS: M+=490. CHN: calc'd: C, 73.59; H, 8.03; N, 8.58. Found: C, 73.68; H, 7.92; N;8.24.

Example 10

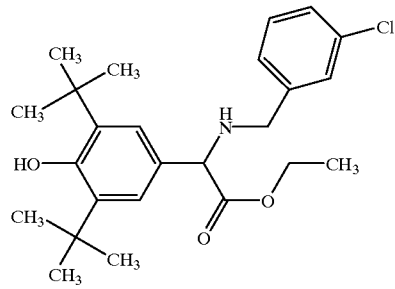

(3-Chloro-benzylamino)-(3,5-di-tert-butyl-4-hydroxy-phenyl)-acetic acid ethyl ester Synthesized as in Example 2 from Intermediate 3 (585 mg, 1.91 mmol) and 3-chlorobenzaldehyde (282 mg, 2.01 mmol). This gave 0.54 g (65%) of product.

MS: M+=432. CHN: calc'd: C, 69.51; H, 7.93; N, 3.24. Found: C, 69.55; H, 8.13; N, 3.31.

Example 11

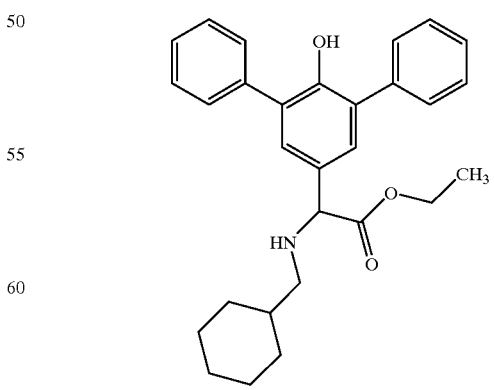

(Cyclohexylmethyl-amino)-(2'-hydroxy-[1,1';3',1"]terphenyl-5'-yl)-acetic acid ethyl ester Synthesized as in Example 2 from Intermediate 6 (350 mg, 1.0 mmol) and cyclohexyl carboxaldehyde (112 mg, 1.0 mmol). This gave 0.33 g (75%) of product.

MS: M+=443. CHN: calc'd (for 0.15 H$_2$O): C, 77.73; H, 7.54; N, 3.12. Found: C, 77.75; H, 7.63; N, 2.95.

Example 12

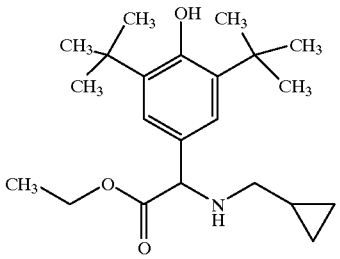

(Cyclopropylmethyl-amino)-(3,5-di-tert-butyl-4-hydroxyphenyl)-acetic acid ethyl ester Synthesized as in Example 2 from Intermediate 3 (1.03 g, 3.0 mmol) and cyclopropyl carboxaldehyde (217 mg, 3.1 mmol). This gave 0.435 g (42%) of product.

MS: M+=361. CHN: calc'd: C, 73.09; H, 9.76; N, 3.87. Found: C, 72.87; H, 9.79; N, 3.83.

Example 13

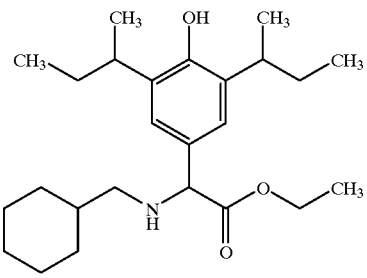

(Cyclohexylmethyl-amino)-(3,5-di-sec-butyl-4-hydroxyphenyl)-acetic acid ethyl ester Synthesized as in Example 2 from Intermediate 9 (0.800 g, 2.6 mmol) and cyclohexyl carboxaldehyde (224 mg, 2.0 mmol). This gave 0.175 g (22%) of product.

MS: M+=404. CHN: calc'd: C, 68.23; H, 9.62; N, 3.18. Found: C, 66.43; H, 9.52; N, 3.78. HPLC (C18, 1:1 (water:CH$_3$CN), 1.0 mL/min, λ=254 nM): 94%.

Example 14

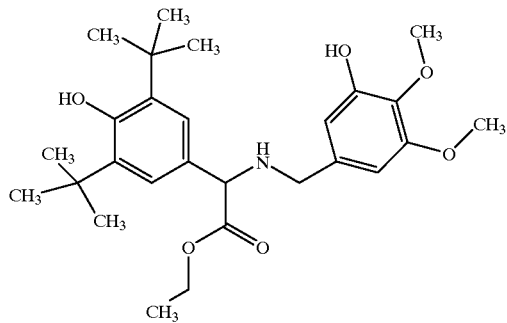

(3,5-Di-tert-butyl-4-hydroxy-phenyl)-(3-hydroxy-4,5-dimethoxy-benzylamino)-acetic acid ethyl ester Synthesized as in Example 2 from Intermediate 3 (0.550 g, 1.6 mmol) and 3,4-dimethoxy-5-hydroxy benzaldehyde (304 mg, 1.67 mmol). This gave 0.40 g (53%) of product.

MS: M+=474. CHN: calc'd: C, 68.47; H, 8.30; N, 2.96. Found: C, 68.37; H, 8.33; N, 2.89.

Example 15

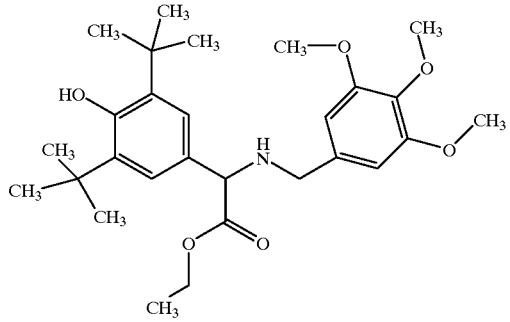

(3,5-Di-tert-butyl-4-hydroxy-phenyl)-(3,4,5-trimethoxy-benzylamino)-acetic acid ethyl ester Synthesized as in Example 2 from Intermediate 3 (0.55 g, 1.6 mmol) and 3,4,5-trimethoxy benzaldehyde (0.329 mg, 1.68 mmol). This gave 0.3 g (40%) of product.

MS: M+=488. CHN: calc'd: C, 68.97; H, 8.47; N, 2.87. Found: C, 68.96; H, 8.45; N, 2.80.

Example 16

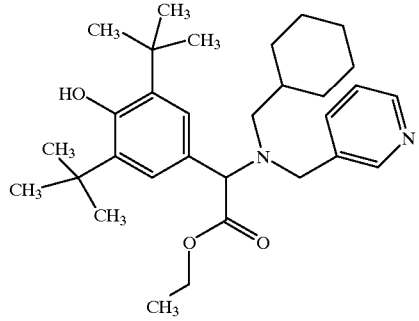

(Cyclohexylmethyl-pyridin-3-ylmethyl-amino)-(3,5-di-tert-butyl-4-hydroxy-phenyl)-acetic acid ethyl ester Synthesized as in Example 2 from Example 2 (0.418 g, 1.05 mmol) and cyclohexyl carboxaldehyde (384 μL, 3.10 mmol). This gave 0.120 g (24%) of product.

MS: M+=495. CHN: calc'd: C, 75.26; H, 9.37; N, 5.66. Found: C, 75.03; H, 9.30; N, 5.50.

Example 17

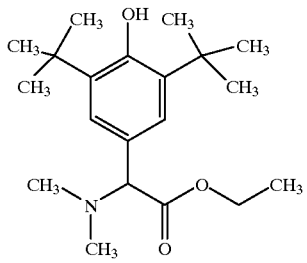

(3,5-Di-tert-butyl-4-hydroxy-phenyl)-dimethylamino-acetic acid ethyl ester

To a THF (25 mL) solution of crude Intermediate 11 (2.2 g, 5.93 mmol) was added dimethyl amine gas, charged for 5 minutes. The mixture was then stirred for 3.5 hours and evaporated in vacuo to give a semi-solid. This was dissolved in methylene chloride (100 mL) and washed with water (100 mL). The organic phase was separated, washed with brine (100 mL), and dried over magnesium sulfate. The solvents were evaporated in vacuo to give an oil which was purified by chromatography (200 g flash silica gel, 1:3 (ethyl acetate:hexane). The appropriate fractions were combined and evaporated in vacuo to give 0.845 (43%) of product as a white solid.

MS: $M^+$=336. CHN: calc'd: C, 71.60; H, 9.91; N, 4.17. Found: C, 71.56; H, 9.97; N, 4.07.

Example 18

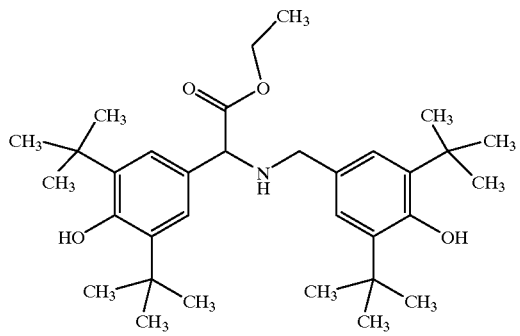

(3,5-Di-tert-butyl-4-hydroxy-phenyl)-[(3,5-Di-tert-butyl-4-hydroxy-phenyl)methyl)-amino]-acetic acid ethyl ester Synthesized as in Example 2 from Intermediate 3 (1.0 g, 3.25 mmol) and 3,5-di-t-butyl-4-hydroxy-benzaldehyde (0.76 g, 3.25 mmol). This gave 0.6 g (35%) of the product.

MS: $M^+$=525. CHN: calc'd (.$H_2O$): C, 72.89; H, 9.75; N, 2.57. Found: C, 72.71; H, 9.82; N, 2.36

Example 19

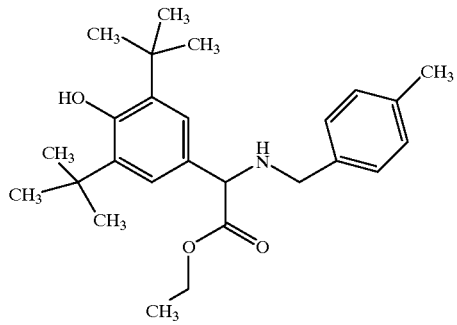

(3,5-Di-tert-butyl-4-hydroxy-phenyl)-[methyl-(4-methyl-benzyl)-amino]-acetic acid ethyl ester Synthesized as in Example 2 from Intermediate 3 (0.550 g, 1.60 mmol) and 4-methylbenzaldehyde (198 µL, 1.63 mmol). This gave 0.38 g (58%) of pure product.

MS: $M^+$=412. CHN: calc'd: C, 75.87; H, 9.06; N, 3.40. Found: C, 75.95; H, 8.79; N, 3.36.

Example 20

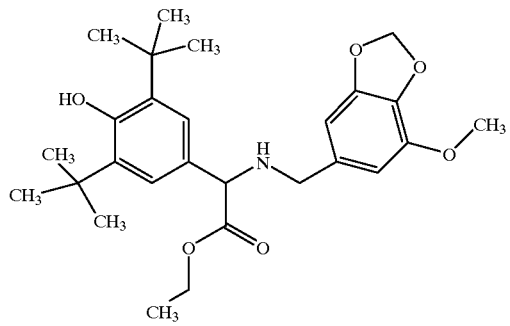

(3,5-Di-tert-butyl-4-hydroxy-phenyl)-[(7-methoxy-benzo[1,3]dioxol-5-ylmethyl)-amino]-acetic acid ethyl ester Synthesized as in Example 2 from Intermediate 3 (0.550 g, 1.60 mmol) and 3-methoxy-4,5-methylene dioxy-benzaldehyde (302 mg, 1.68 mmol). This gave 0.33 g (44%) of pure product.

MS: $M^+$=472. CHN: calc'd: C, 68.77; H, 7.91; N, 2.97. Found: C, 68.61; H, 7.97; N, 2.90.

Example 21

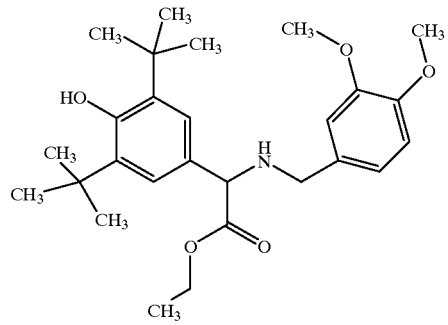

(3,5-Di-tert-butyl-4-hydroxy-phenyl)-(3,4-dimethoxy-benzylamino)-acetic acid ethyl ester Synthesized as in Example 2 from Intermediate 3 (0.550 g, 1.60 mmol) and 3,4-dimethoxybenzaldehyde (282 mg, 1.70 mmol). This gave 0.28 g (38%) of the product.

MS: M⁺=458. CHN: calc'd: C, 70.87; H, 8.59; N, 3.06. Found: C, 70.60; H, 8.26; N, 2.92.

Example 22

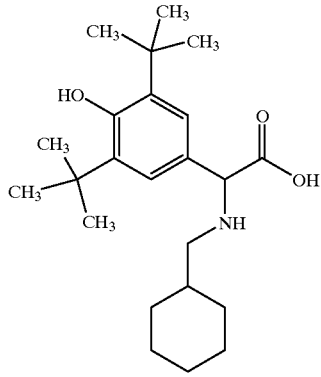

(Cyclohexylmethyl-amino)-(3,5-di-tert-butyl-4-hydroxy-phenyl)-acetic acid

Synthesized as in Example 7 from Example 6 (1.1 g, 2.73 mmol). This gave 0.73 g (73%) of the product acid.

Example 23

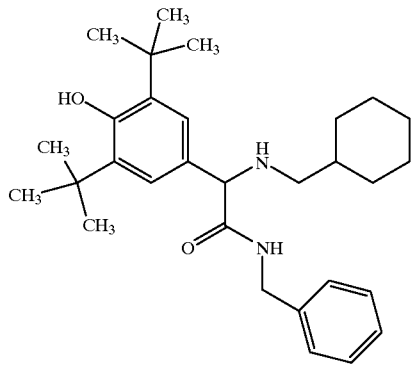

N-Benzyl-2-(cyclohexylmethyl-amino)-2-(3,5-di-tert-butyl-4-hydroxy-phenyl)-acetamide To a methylene chloride (5 mL) solution of Example 22 (0.36 g, 0.96 mmol) was added benzyl amine (110 mg, 1.0 mmol), N,N¹-dicyclohexylcarbodiimide (DCC) (206 mg, 1.0 mmol), and 1-hydroxybenzotriazole (HOBT) (135 mg, 1.0 mmol). The solution was stirred at room temperature for 24 hours. The mixture was filtered free of insolubles and the filtrate evaporated to give an oil. The oil was dissolved in methanol (30 mL) treated with charcoal and evaporated to a foam. The foam was dissolved in ethyl acetate (75 mL) and washed with saturated sodium bicarbonate (50 mL) and then dried over magnesium sulfate. This was purified by chromatography (125 g silica gel, 2% methanol in methylene chloride). The appropriate fractions were combined and evaporated in vacuo to give 0.10 g (22%) of product.

MS: M⁺=465. CHN: calc'd: C, 77.54; H, 9.54; N, 6.03. Found: C, 77.12; H, 9.68; N, 6.10.

Example 24

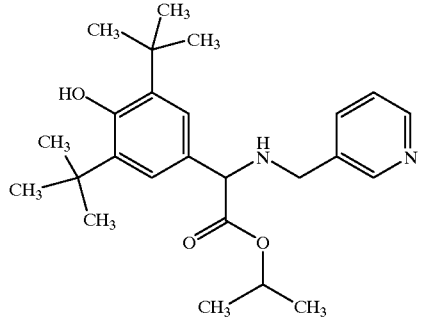

(3,5-Di-tert-butyl-4-hydroxy-phenyl)-[(pyridin-3-ylmethyl)-amino]-acetic acid isopropyl ester Synthesized as in Example 2 from Intermediate 15 (0.455 g, 1.42 mmol) and 3-pyridine carboxaldehyde (142 μL, 1.50 mmol). This gave 0.362 g (62%) of the product.

MS: M⁺=413. CHN: calc'd: C, 72.78; H, 8.80; N, 6.74. Found: C, 72.61; H, 8.88; N, 6.45.

Example 25

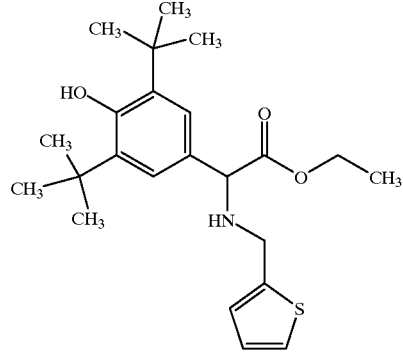

(3,5-Di-tert-butyl-4-hydroxy-phenyl)-[(thiophen-2-ylmethyl)-amino]-acetic acid ethyl ester Synthesized as in Example 2 from Intermediate 3 (0.614 g 2.0 mmol) and 2-thiophene carboxaldehyde (235 mg, 2.1 mmol). This gave 0.440 g (55%) of the product.

MS: M⁺=404. CHN: calc'd: C, 68.45; H, 8.24; N, 3.47. Found: C, 68.49; H, 8.04; N, 3.39.

Example 26

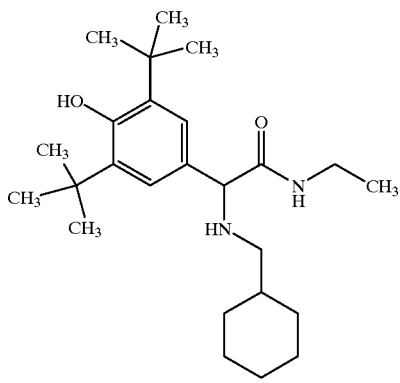

2-(Cyclohexylmethyl-amino)-2-(3,5-di-tert-butyl-4-hydroxy-phenyl)-N-ethyl-acetamide Synthesized as in Example 23 from Example 22 (0.57 g, 1.52 mmol) and ethyl amine (836 μL, 1.67 mmol). This gave 0.120 g (20%) of the product.

MS: M$^+$=403. CHN: calc'd (0.2 H$_2$O): C, 73.91; H, 10.52; N, 6.90. Found: C, 73.9 1; H, 10.52; N, 6.90.

Example 27

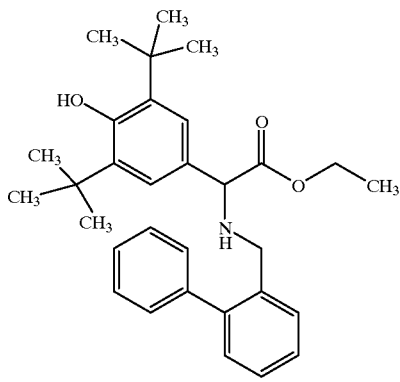

(3,5-Di-tert-butyl-4-hydroxy-phenyl)-[(2-phenyl-phenylmethyl)-amino]-acetic acid ethyl ester Synthesized as in Example 2 from Intermediate 3 (0.614 g, 2.0 mmol) and 2-phenyl benzaldehyde (383 mg, 2.1 mmol). This gave 0.120 g (13%) of the product.

MS: M$^+$=474. CHN: calc'd: C, 78.61; H, 8.30; N, 2.96. Found: C, 78.72; H, 8.26; N, 2.87.

Example 28

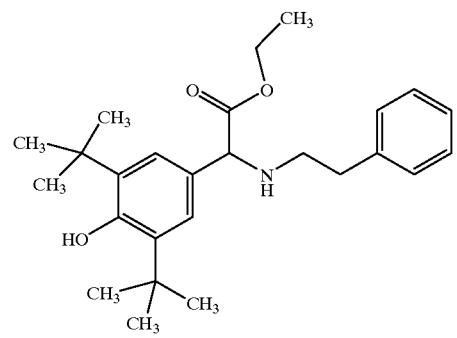

(3,5-Di-tert-butyl-4-hydroxy-phenyl)-phenethylamino-acetic acid ethyl ester

Synthesized as in Example 2 from Intermediate 3 (0.614 g, 2.0 mmol) and phenyl acetaldehyde (264 mg, 2.1 mmol). This gave 0.320 g (39%) of the product.

MS: M$^+$=412. CHN: calc'd: C, 75.87; H, 9.06; N, 3.40. Found: C, 75.86; H, 8.81; N, 3.28.

Example 29

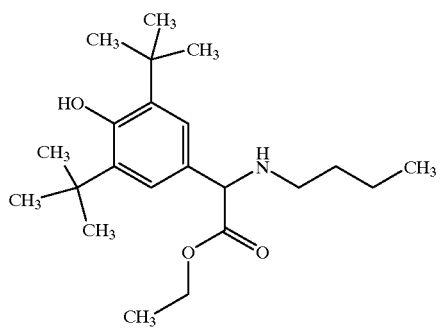

(3,5-Di-tert-butyl-4-hydroxy-phenyl)-[(butyl)-amino]-acetic acid ethyl ester

Synthesized as in Example 2 from Intermediate 3 (0.614 g, 2.0 mmol) and butyraldehyde (151 mg, 2.1 mmol). This gave 0.365 g (50%) of the product.

MS: M$^+$=364. CHN: calc'd: C, 72.68; H, 10.26; N, 3.85. Found: C, 72.83; H, 10.10; N, 3.76.

Examples 30–57

These derivatives were synthesized via a combinatorial approach in a manner similar to that used for Example 2. The approach used 0.1 mmol of Intermediate 3, 0.11 mmol of the aldehyde, and 0.14 mmol of sodium triacetoxy borohydride.

Purity of these derivatives was determined by HPLC/MS techniques.

HPLC conditions: C18 column, 150 mm×4.6 mm, 5μ; 1:1 (0.1% TFA/H$_2$0:0.1% TFA/CH$_3$CN); 1 mL/min; λ=214 nm. MS: APCI$^\oplus$.

Example 30

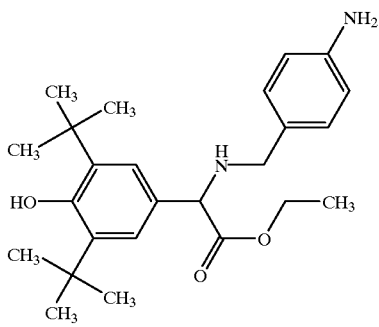

(4-Amino-benzylamino)-(3,5-di-tert-butyl-4-hydroxy-phenyl)-acetic acid ethyl ester From 4-aminobenzaldehyde was isolated the product.
MS: M$^+$=413.2, HPLC, 48%.

Example 31

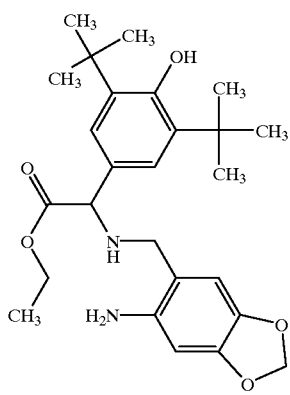

[(6-Amino-benzo[1,3]dioxol-5-ylmethyl)-amino]-(3,5-di-tert-butyl-4-hydroxy-phenyl)-acetic acid ethyl ester From 2-amino-4,5-methylenedioxybenzaldehyde was isolated the product.
MS: M$^+$=457.20, HPLC, 38.7%.

Example 32

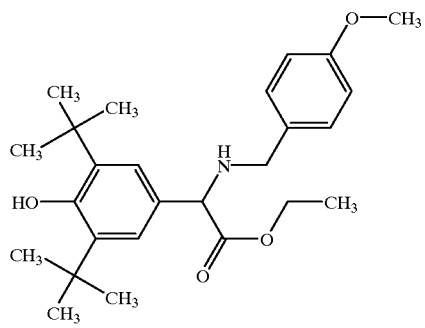

(3,5-Di-tert-butyl-4-hydroxy-phenyl)-(4-methoxy-benzylamino)-acetic acid ethyl ester From 4-methoxybenzaldehyde was isolated the product.
MS: M$^+$=428.20, HPLC, 86.2%.

Example 33

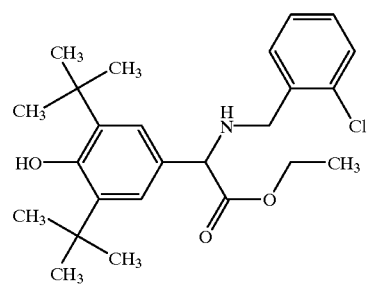

(2-Chloro-benzylamino)-(3,5-di-tert-butyl-4-hydroxy-phenyl)-acetic acid ethyl ester From 2-chlorobenzaldehyde was isolated the product.
MS: M$^+$=432.20, HPLC, 89.8%.

Example 34

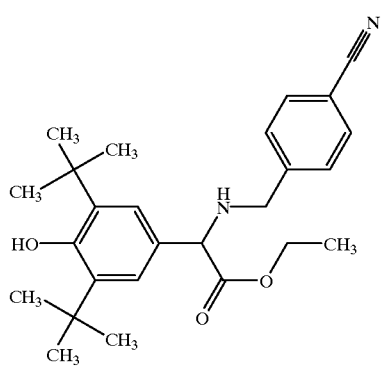

(4-Cyano-benzylamino)-(3,5-di-tert-butyl-4-hydroxy-phenyl)-acetic acid ethyl ester From 4-cyanobenzaldehyde was isolated the product.
MS: M$^+$=423.20, HPLC, 87.6%.

Example 35

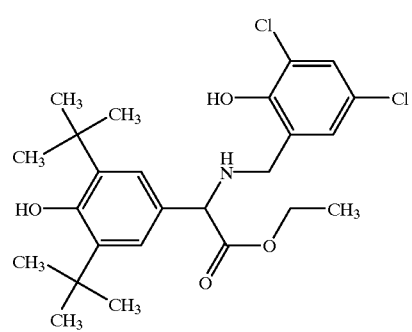

(3,5-Di-tert-butyl-4-hydroxy-phenyl)-(3,5-dichloro-2-hydroxy-benzylamino)-acetic acid ethyl ester From 3,5-dichloro-2-hydroxybenzaldehyde was isolated the product.
MS: M$^+$=482.10, HPLC, 91.9%.

Example 36

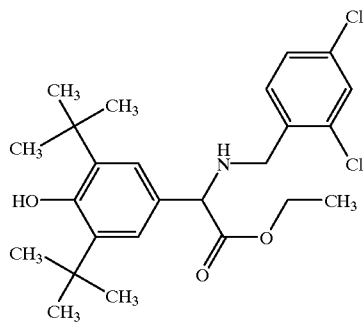

(3,5-Di-tert-butyl-4-hydroxy-phenyl)-(2,4-dichloro-benzylamino)-acetic acid ethyl ester From 2,4-dichlorobenzaldehyde was isolated the product.
MS: $M^+$=466.10, HPLC, 87.4%.

Example 37

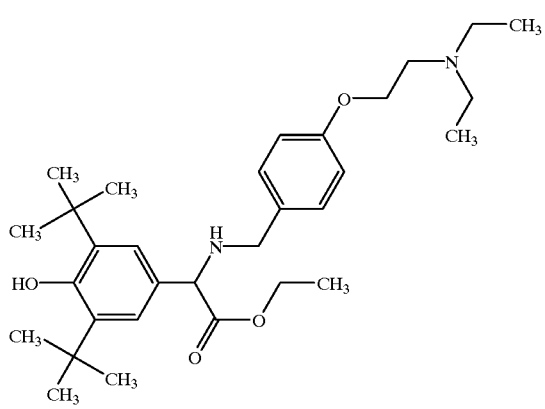

(3,5-Di-tert-butyl-4-hydroxy-phenyl)-[4-(2-diethylamino-ethoxy)-benzylamino]-acetic acid ethyl ester From 4-2-(diethylamino)ethoxybenzaldehyde was isolated the product.
MS: $M^+$=513.30, HPLC, 74.4%.

Example 38

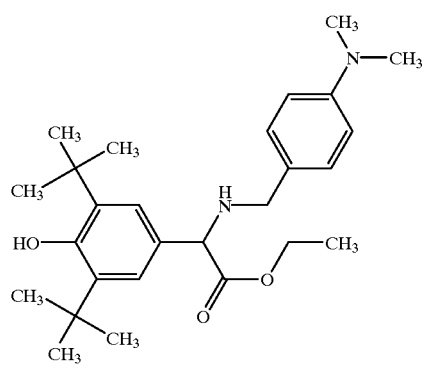

(3,5-Di-tert-butyl-4-hydroxy-phenyl)-[4-dimethylamino-benzylamino]-acetic acid ethyl ester From 4-dimethylaminobenzaldehyde was isolated the product.
MS: $M^+$=441.30, HPLC, 80.89%.

Example 39

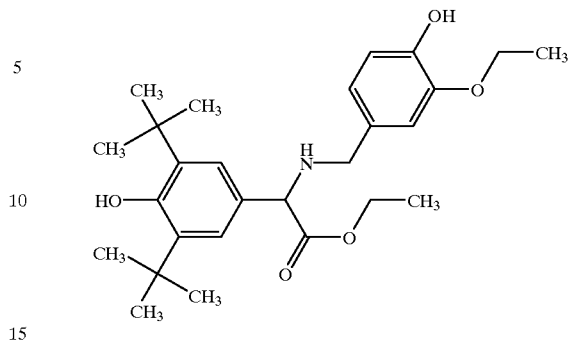

(3,5-Di-tert-butyl-4-hydroxy-phenyl)-(3-ethoxy-4-hydroxy-benzylamino)-acetic acid ethyl ester From 4-hydroxy-3-ethoxybenzaldehyde was isolated the product.

MS: $M^+$=458.20, HPLC, 97.6%.

Example 40

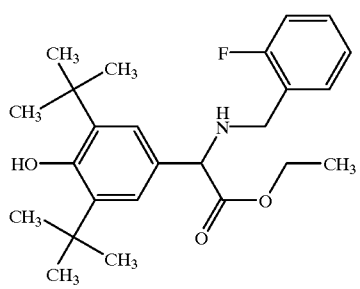

(3,5-Di-tert-butyl-4-hydroxy-phenyl)-(2-fluoro-benzylamino]-acetic acid ethyl ester From 2-flurorbenzaldehyde was isolated the product.

MS: $M^+$=416.20, HPLC, 75.9%.

Example 41

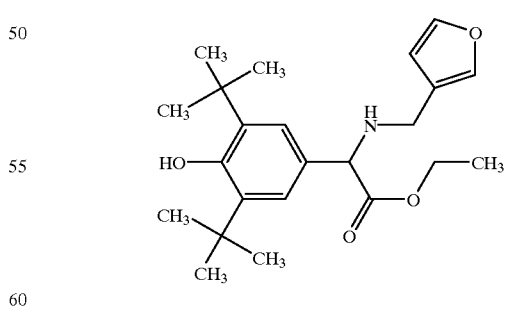

(3,5-Di-tert-butyl-4-hydroxy-phenyl)-[(furan-3-ylmethyl)-amino]-acetic acid ethyl ester From 3-furanecarboxaldehyde was isolated the product.

MS: $M^+$=388.20, HPLC, 73%.

Example 42

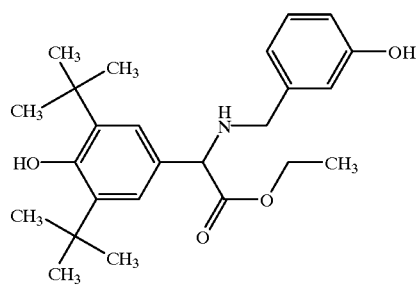

(3,5-Di-tert-butyl-4-hydroxy-phenyl)-(3-hydroxy-benzylamino)-acetic acid ethyl ester From 3-hydroxybenzaldehyde was isolated the product.

MS: $M^+$=414.20, HPLC, 88.6%.

Example 43

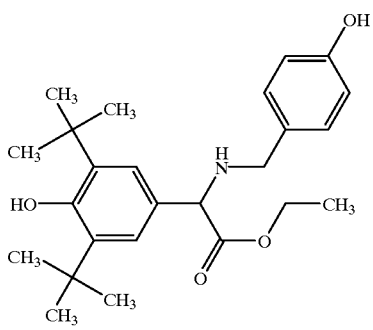

(3,5-Di-tert-butyl-4-hydroxy-phenyl)-(4-hydroxy-benzylamino)-acetic acid ethyl ester From 4-hydroxybenzaldehyde was isolated the product.

MS: $M^+$=419.20, HPLC, 91.8%.

Example 44

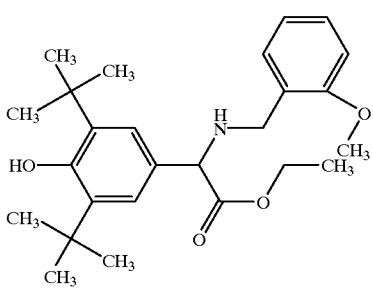

(3,5-Di-tert-butyl-4-hydroxy-phenyl)-(2-methoxy-benzylamino)-acetic acid ethyl ester From 2-methoxybenzaldehyde was isolated the product.

MS: $M^+$=428.20, HPLC, 93.1%.

Example 45

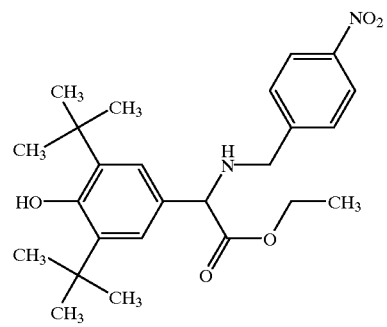

(3,5-Di-tert-butyl-4-hydroxy-phenyl)-(4-nitro-benzylamino)-acetic acid ethyl ester From 4-nitrobenzaldehyde was isolated the product.

MS: $M^+$=443.20, HPLC, 78.3%.

Example 46

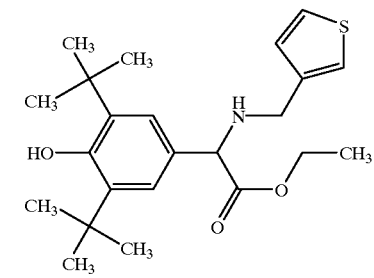

(3,5-Di-tert-butyl-4-hydroxy-phenyl)-[(thiophen-3-ylmethyl)-amino]-acetic acid ethyl ester From 3-thiophenecarboxaldehyde was isolated the product.

MS: $M^+$=404.20, HPLC, 100%.

Example 47

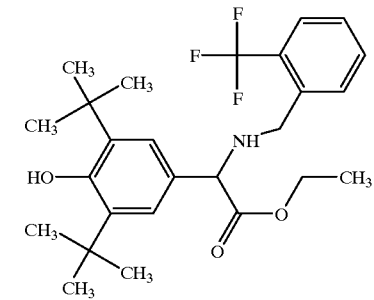

(3,5-Di-tert-butyl-4-hydroxy-phenyl)-(2-trifluoromethyl-benzylamino)-acetic acid ethyl ester From 2-trifluoromethylbenzaldehyde was isolated the product.

MS: $M^+$=466.20, HPLC, 77.0%.

Example 48

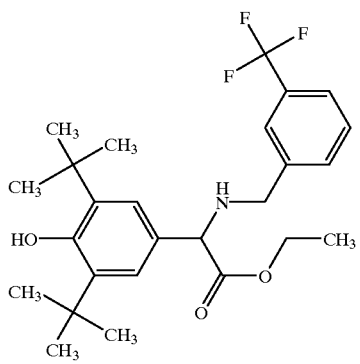

(3,5-Di-tert-butyl-4-hydroxy-phenyl)-(3-trifluoromethyl-benzylamino)-acetic acid ethyl ester From 3-trifluoromethylbenzaldehyde was isolated the product.

MS: $M^+$=466.20, HPLC, 89.0%.

Example 49

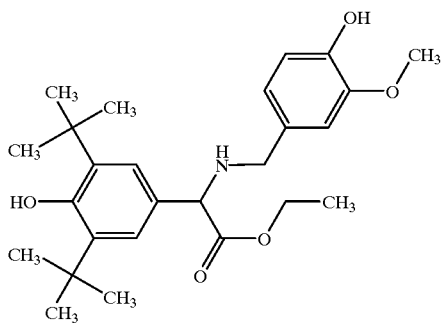

(3,5-Di-tert-butyl-4-hydroxy-phenyl)-(4-hydroxy-3-methoxy-benzylamino)-acetic acid ethyl ester From 3-methoxy-4-hydroxybenzaldehyde was isolated the product.

MS: $M^+$=444.20, HPLC, 93.6%.

Example 50

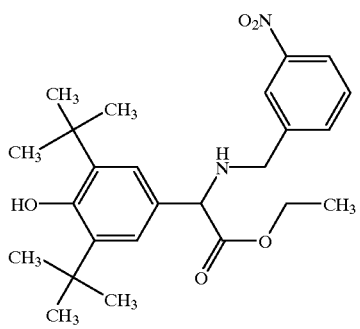

(3,5-Di-tert-butyl-4-hydroxy-phenyl)-(3-nitro-benzylamino)-acetic acid ethyl ester From 3-nitrobenzaldehyde was isolated the product.
MS: $M^+$=443.20, HPLC, 83.1%.

Example 51

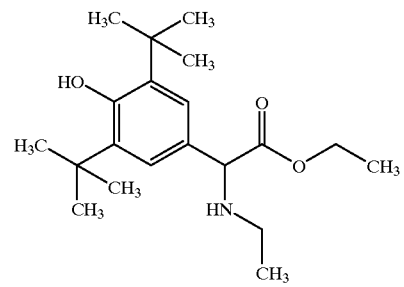

(3,5-Di-tert-butyl-4-hydroxy-phenyl)-(ethylamino)-acetic acid ethyl ester

In the THF (35 mL) was dissolved intermediate 17 (1.51 g, 5.2 mmol) and to this was added a solution of ethyl amine (6 mL of a 2N solution in THF, 12 mmol). The mixture stirred at room temperature for 10 minutes. The material evaporated in vacuo and partitioned between methylene chloride (100 mL) and water (100 mL). The organic phase separated, washed with brine and dried over magnesium sulfate. The solvent was evaporated in vacuo to give a solid. The compound was purified by chromatography (150 g flash silica gel, 3:1 [hexane:ethyl acetate]). The appropriate fractions were combined and evaporated in vacuo to give 1.0 g (57%) of the pure compound.

MS: $M^+$=336. Microanalysis ($C_{20}H_{33}NO_3$): calc'd: C, 71.60; H, 9.91; N, 4.17. Found: C, 71.91; H, 9.99; N, 4.11.

Example 52

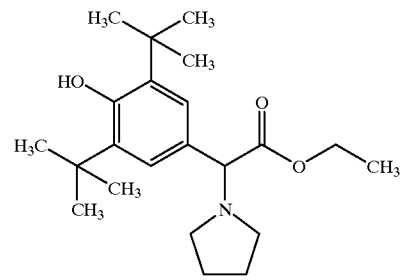

(3,5-Di-tert-butyl-4-hydroxy-phenyl)-(N-pyrollidinyl)-acetic acid ethyl ester

Synthesized as in Example 51 from Intermediate 17 (0.54 g, 1.86 mmol) and pyrollidine (284 mg, 4.0 mmol). This gave 0.415 mg (62%) of product.

MS: $M^+$=362. Microanalysis ($C_{22}H_{35}NO_3$): calc'd: C, 73.09; H, 9.76; N, 3.87. Found: C, 73.25; H, 9.71; N, 3.70.

Example 53

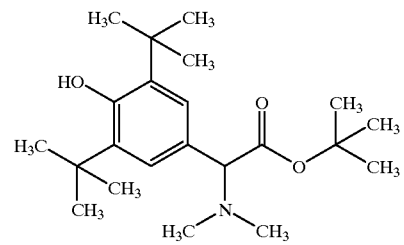

(3,5-Di-tert-butyl-4-hydroxy-phenyl)-dimethylamino-acetic acid t-butyl ester

To a solution of Intermediate 19 (0.8654 g, 2.17 mmol) in 8 mL, THF was bubbled in dimethylamine. The reaction was stirred at ambient temperature overnight. The solvent was removed in vacuo. The residue was taken up in ethyl acetate, washed with brine, dried over MgSO$_4$, and concentrated. The crude product was chromatographed on silica eluting with 5% to 20% EtOAc/hex. The resulting yellow oil crystallized to a yellow solid under high vacuum overnight (28%); mp 74–76° C. MS(APCI/M$^+$): 365.1. CHN: calc'd: C, 72.69; H, 10.26; N, 3.85. Found: C, 72.57; H, 9.52; N, 3.57.

Example 54

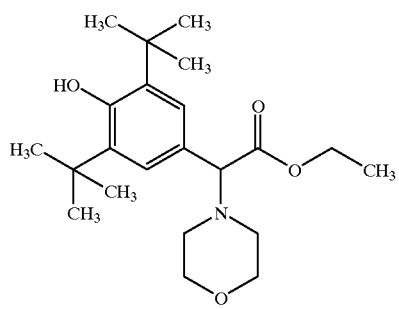

(3,5-Di-tert-butyl-4-hydroxy-phenyl)-(N-morpholinyl)-acetic acid ethyl ester

The compound was synthesized as in Example 17 from Intermediate 11 (4.0 g, 10.8 mmol) and morpholine (2.1 g, 24 mmol). This gave 0.91 g (22%) of pure product.

MS: M$^+$=378. CHN: calc'd: C, 69.99; H, 9.34; N, 3.71. Found: C, 69.94; H, 9.23; N, 3.61.

Example 55

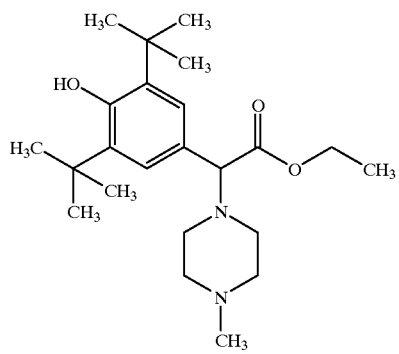

(3,5-Di-tert-butyl-4-hydroxy-phenyl)-[(N'-methyl)-N-piperazinyl]-acetic acid ethyl ester The compound was synthesized as in Example 17 from Intermediate 11 (2.3 g, 6.2 mmol) and N-methylpiperazine (1.60 g, 16 mmol). This gave 1.1 g (46%) of pure product.

MS: M$^+$=391. CHN: calc'd: C, 70.73; H, 9.81; N, 7.17. Found: C, 69.54; H, 9.67; N, 7.18.

Example 56

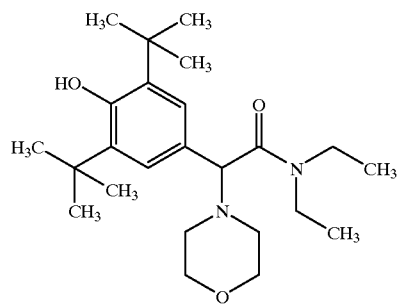

Diethyl-(3,5-Di-tert-butyl-4-hydroxy-phenyl)-(N-morpholinyl)-acetamide

Synthesized as in Example 51 from Intermediate 21 (1.84 g, 5.8 mmol) and morpholine (1.06 g, 12.2 mmol). This gave 1.65 g (70%) of pure product.

MS: M$^+$=405. CHN: calc'd: C, 71.25; H, 9.97; N, 6.92. Found: C, 70.97; H, 9.79; N, 6.82.

Example 57

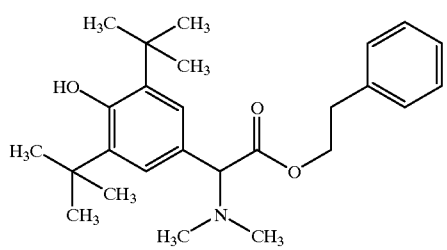

(3,5-Di-tert-butyl-4-hydroxy-phenyl)-dimethylamino-acetic acid, 2-phenylethyl ester Synthesized as in Example 51 from Intermediate 23 (1.3 g, 3.5 mmol) and dimethyl amine (3.75 mL of a 2N solution in THF, 7.5 mmol). This gave 0.915 g (64%) of pure product.

MS: M$^+$=412. CHN: calc'd: C, 75.87; H, 9.06; N, 3.40. Found: C, 76.17; H, 9.22; N, 3.46.

BIOLOGICAL METHODS

LPABC Screen

Purpose

The lipoprotein(a), [Lp(a)], biochemical coupling assay (LPABC) is used to characterize inhibitors of the apolipoprotein(a), [apo(a)], apolipoproteinB-100, [apoB-100], coupling reaction that generates Lp(a).

Protocol Conditioned media from 293 cells (ATCC CRL-1573), permanently transfected with an apo(a) 17-kringle cDNA expression construct (pcDNA-AMP, In Vitrogen, Carlsbad, Calif.) using standard molecular biology techniques, was used as a source of recombinant apo(a). The 293 cell conditioned media containing the recombinant apo(a) is diluted 1:3 with phosphate buffered saline (PBS) and 90 µL is pipetted into each well of a 96-well plate and placed into a 37° C. incubator for 10 minutes. Twenty microliters of a 0.3 to 50 µM solution of a compound of the present invention in PBS is added to the warmed plate. Ninety microliters of HepG2 (ATCC HB-8065) cell conditioned media diluted 1:3 with PBS is added to the apo(a)/compound mixture and mixed by pipetting up and down 5 times. The reaction is incubated for 67 minutes in a 37° C. incubator. A 100 µL aliquot of the reaction is removed and assayed for its Lp(a) content by an enzyme linked immunosorbent assay (ELISA).

LPA3 Screen

Purpose

The LPA3 screen is used to identify compounds that inhibit Lp(a) production. This screen employs permanently transfected HepG2 cells (HepG2$^{K17}$) that are generated using an apo(a) 17-kringle cDNA expression construct (pcDNA-AMP, In Vitrogen, Carlsbad, Calif.) in accordance with methods that are well-known in molecular biology.

Protocol

HepG2$^{K17}$ cells are seeded in 96-well plates at a density of 75,000 cells per well in 0.25 mL of Dulbecco's Modified Eagle Media (DMEM) containing 10% fetal bovine serum (FBS). Seeded plates are incubated overnight in a 37° C., 5% $CO_2$/95% $O_2$ incubator. The media is removed, replaced with (1) fresh media, or (2) fresh media plus 0.3 to 50 μM of a compound of the present invention in 20 μL of PBS, and the plates returned to the incubator for 8 hours. After the additional 8 hours of incubation, Lp(a) is assayed in the media by ELISA. Cells are digested with 0.5N NaOH overnight and assayed for total protein. Lp(a) values are normalized for total protein content.

| Example No. | LPABC IC$_{50}$ μM | LPA3 IC$_{50}$ ↑M |
|---|---|---|
| 1 | 6.48 | 7.6 |
| 2 | 10 | 20 |
| 3 | 7.27 | 25.4 |
| 4 | 6.48 | 9.1 |
| 5 | 10.27 | 76 |
| 6 | 6.52 | >74 |
| 7 | 62.22 | |
| 8 | 4.16 | 49.2,18.7[a] |
| 9 | 1.34/1.3[a] | 2.42/5.2/3.9[a] |
| 10 | 12.48 | |
| 11 | 60.18 | |
| 12 | 12.17 | |
| 13 | 67.39 | |
| 14 | 10.56 | 9.3 |
| 15 | 10.26 | 4.6 |
| 16 | 1.48 | 3.7 |
| 17 | 0.65 | |
| 18 | 75.04 | |
| 30 | 62.61 | >74 |
| 31 | 20.97 | >74 |
| 32 | 29.63 | >74 |
| 33 | 43.40 | >74 |
| 34 | 57.64 | >74 |
| 35 | 15.87 | >74 |
| 36 | 47.94 | >74 |
| 37 | 29.61 | |
| 38 | 53.99 | >74 |
| 39 | 59.08 | >74 |
| 40 | 50.16 | >74 |
| 41 | 9.37[a] | |
| 42 | 68.38 | >74 |
| 43 | 29.18 | >74 |
| 44 | 54.30 | >74 |
| 45 | 96.83 | >74 |
| 46 | 34.47 | >74 |
| 47 | 33.41 | >74 |
| 48 | 53.94 | >74 |
| 49 | 14.98 | >74 |
| 50 | 46.68 | >74 |
| 51 | 10.9 | |
| 52 | 1.55 | 2.7 |
| 54 | 0.8 | 1.3 |
| 55 | 1.66 | |
| 56 | 1.17 | |

[a]Multiple tests.

What is claimed is:

1. Compounds having the Formula I

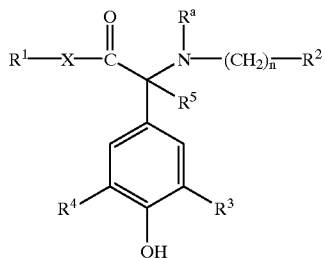

wherein each $R^1$ is independently hydrogen or $C_1$–$C_6$ alkyl;

$R^2$ is heteroaryl, substituted heteroaryl, aryl, substituted aryl, $C_3$–$C_8$ cycloalkyl, or substituted $C_3$–$C_8$ cycloalkyl;

X is —O— or

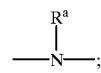

each $R^3$ and $R^4$ is independently $C_1$–$C_6$ alkyl —O$C_1$–$C_6$ alkyl, or phenyl;

$R^a$ is hydrogen, $C_1$–$C_6$ alkyl, —(CH$_2$)$_n$-heteroaryl, —(CH$_2$)$_n$-substituted heteroaryl, —(CH$_2$)$_n$aryl, —(CH$_2$)$_n$-substituted aryl, —(CH$_2$)$_n$—$C_3$–$C_8$ cycloalkyl, —(CH$_2$)$_n$ substituted $C_3$–$C_8$ cycloalkyl, or $R^a$ and $R^2$ taken together with the N and any —(CH$_2$)$_n$— form a ring structure comprised of from 4 to 8 atoms and including 1 or 2 heteroatoms;

each n is independently 0, 1, 2, or 3;

$R^5$ is hydrogen or $C_1$–$C_6$ alkyl;

and the pharmaceutically acceptable salts thereof.

2. A compound in accordance with claim 1 wherein X is —O—.

3. A compound in accordance with claim 1 wherein $R^1$ is —CH$_2$CH$_3$.

4. A compound in accordance with claim 1 wherein $R^a$ is hydrogen.

5. A compound in accordance with claim 1 wherein $R^3$ and $R^4$ are

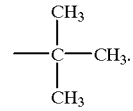

6. A compound in accordance with claim 1 wherein $R^2$ is pyridyl.

7. A compound in accordance with claim 1 wherein X is —O—;

$R^1$ is —CH$_2$CH$_3$;

$R^a$ is hydrogen; and

R³ and R⁴ are

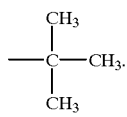

8. A compound in accordance with claim 1 wherein R² is pyridyl, phenyl, substituted phenyl, cyclohexyl, cyclopropyl, furyl, or thienyl.

9. Compounds having the Formula I

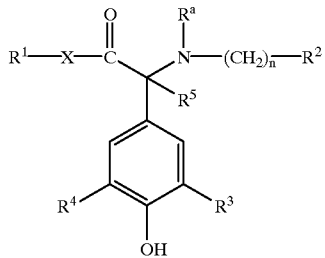

wherein each R¹ is independently hydrogen or ethyl;

R² is pyridyl, phenyl, substituted phenyl, cyclohexyl, cyclopropyl, furyl, or thienyl;

X is —O— or

R³ and R⁴ are each

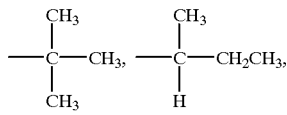

or phenyl;

R⁵ is hydrogen;

Rᵃ is hydrogen or C₁–C₆ alkyl;

n is 0 or 1; and the pharmaceutically acceptable salts thereof.

10. A compound in accordance with claim 9 wherein R² is substituted phenyl and the substituents are selected from the group —NH₂, —N(CH₃)₂,

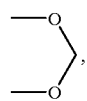

—OCH₃, —OCH₂CH₃, —F, —Cl, —NO₂, —CF₃, —CN, —OH, and —OCH₂CH₂N(CH₂CH₃)₂.

11. A compound in accordance with claim 9 wherein X is —O—,

R⁴ and R³ are

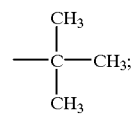

Rᵃ and R² are —CH₃; and n is O.

12. The compounds:
(3,5-Di-tert-butyl-4-hydroxy-phenyl)-[(pyridin-3-yl)-amino]-acetic acid ethyl ester;
(3,5-Di-tert-butyl-4-hydroxy-phenyl)-[(pyridin-4-ylmethyl)-amino]-acetic acid ethyl ester;
(3,5-Di-tert-butyl-4-hydroxy-phenyl)-[(pyridin-4-ylmethyl)-amino]-acetic acid ethyl ester;
(3,5-Di-tert-butyl-4-hydroxy-phenyl)-[pyridin-2-ylmethyl)-amino]-acetic acid ethyl ester;
Benzylamino-(3,5-di-tert-butyl-4-hydroxy-phenyl)-acetic acid ethyl ester;
(Cyclohexylmethyl-amino)-(3,5-di-tert-butyl-4-hydroxy-phenyl)-acetic acid ethyl ester;
(3,5-Di-tert-butyl-4-hydroxy-phenyl)-[(pyridin-3-ylmethyl)-amino]-acetic acid;
(3,5-Di-tert-butyl-4-hydroxy-phenyl)-[(cyclohexyl)-amino]-acetic acid etyl ester;
(Bis-pyridin-3-ylmethyl-amino)-(3,5-di-tert-butyl-4-hydroxy-phenyl)-acetic acid ethyl ester;
(3-Chloro-benzylamino)-(3,5-di-tert-butyl-4-hydroxy-phenyl)-acetic acid ethyl ester;
(Cyclohexylmethyl-amino)-(2'-hydroxy-[1,1';3',1"]terphenyl-5'-yl)-acetic acid ethyl ester;
(Cyclopropylmethyl-amino)-(3,5-di-tert-butyl-4-hydroxy-phenyl)-acetic acid ethyl ester;
(Cyclohexylmethyl-amino)-(3,5-di-sec-butyl-4-hydroxy-phenyl)-acetic acid ethyl ester;
(3,5-Di-tert-butyl-4-hydroxy-phenyl)-(3-hydroxy-4,5-dimethoxy-benzylamino)-acetic acid ethyl ester;
(3,5-Di-tert-butyl-4-hydroxy-phenyl)-(3,4,5-trimethoxy-benzylamino)-acetic acid ethyl ester;
(Cyclohexylmethyl-pyridin-3-ylmethyl-amino)-(3,5-di-tert-butyl-4-hydroxy-phenyl)-acetic acid ethyl ester;
(3,5-Di-tert-butyl-4-hydroxy-phenyl)-[(3,5-Di-tert-butyl4-hydroxy-phenyl)methyl)-amino]-acetic acid ethyl ester;
(3,5-Di-tert-butyl-4-hydroxy-phenyl)-[methyl-(4-methyl-benzyl)-amino]-acetic acid ethyl ester;
(3,5-Di-tert-butyl-4-hydroxy-phenyl)-[(7-methoxy-benzo[1,3]dioxol-5-ylmethyl)-amino]-acetic acid ethyl ester;
(3,5-Di-tert-butyl-4-hydroxy-phenyl)-(3,4-dimethoxy-benzylamino)-acetic acid ethyl ester;
(Cyclohexylmethyl-amino)-(3,5-di-tert-butyl-4-hydroxy-phenyl)-acetic acid;
N-Benzyl-2-(cyclohexylmethyl-amino)-2-(3,5-di-tert-butyl-4-hydroxy-phenyl)-acetamide;
(3,5-Di-tert-butyl-4-hydroxy-phenyl)-[(pyridin-3-ylmethyl)-amino]-acetic acid isopropyl ester;
(3,5-Di-tert-butyl-4-hydroxy-phenyl)-[(thiophen-2-ylmethyl)-amino]-acetic acid ethyl ester;
2-(Cyclohexylmethyl-amino)-2-(3,5-di-tert-butyl-4-hydroxy-phenyl)-N-ethyl-acetamide;
(3,5-Di-tert-butyl-4-hydroxy-phenyl)-[(2-phenyl-phenylmethyl)-amino]-acetic acid ethyl ester;
(3,5-Di-tert-butyl-4-hydroxy-phenyl)-phenethylamino-acetic acid ethyl ester;
(4-Amino-benzylamino)-(3,5-di-tert-butyl-4-hydroxy-phenyl)-acetic acid ethyl ester;
[(6-Amino-benzo [1,3]dioxol-5-ylmethyl)-amino]-(3,5-di-tert-butyl-4-hydroxy-phenyl)-acetic acid ethyl ester;

(3,5-Di-tert-butyl-4-hydroxy-phenyl)-(4-methoxy-benzylamino)-acetic acid ethyl ester;
(2-Chloro-benzylamino)-(3,5-di-tert-butyl-4-hydroxy-phenyl)-acetic acid ethyl ester;
(4-Cyano-benzylamino)-(3,5-di-tert-butyl-4-hydroxy-phenyl)-acetic acid ethyl ester;
(3,5-Di-tert-butyl-4-hydroxy-phenyl)-(3,5-dichloro-2-hydroxy-benzylamino)-acetic acid ethyl ester;
(3,5-Di-tert-butyl-4-hydroxy-phenyl)-(2,4-dichloro-benzylamino)-acetic acid ethyl ester;
(3,5-Di-tert-butyl-4-hydroxy-phenyl)-[4-(2-diethylamino-ethoxy)-benzylamino]-acetic acid ethyl ester;
(3,5-Di-tert-butyl-4-hydroxy-phenyl)-[4-dimethylamino-benzylamino]-acetic acid ethyl ester;
(3,5-Di-tert-butyl-4-hydroxy-phenyl)-(3-ethoxy-4-hydroxy-benzylamino)-acetic acid ethyl ester;
(3,5-Di-tert-butyl-4-hydroxy-phenyl)-(2-fluoro-benzylamino]-acetic acid ethyl ester;
(3,5-Di-tert-butyl-4-hydroxy-phenyl)-[(furan-3-ylmethyl)-amino]-acetic acid ethyl ester;
(3,5-Di-tert-butyl-4-hydroxy-phenyl)-(3-hydroxy-benzylamino)-acetic acid ethyl ester;
(3,5-Di-tert-butyl-4-hydroxy-phenyl)-(4-hydroxy-benzylamino)-acetic acid ethyl ester;
(3,5-Di-tert-butyl-4-hydroxy-phenyl)-(2-methoxy-benzylamino)-acetic acid ethyl ester;
(3,5-Di-tert-butyl-4-hydroxy-phenyl)-(4-nitro-benzylamino)-acetic acid ethyl ester;
(3,5-Di-tert-butyl-4-hydroxy-phenyl)-[(thiophen-3-ylmethyl)-amino]-acetic acid ethyl ester;
(3,5-Di-tert-butyl-4-hydroxy-phenyl)-(2-trifluoromethyl-benzylamino)-acetic acid ethyl ester;
(3,5-Di-tert-butyl-4-hydroxy-phenyl)-(3-trifluoromethyl-benzylamino)-acetic acid ethyl ester;
(3,5-Di-tert-butyl-4-hydroxy-phenyl)-(4-hydroxy-3-methoxy-benzylamino)-acetic acid ethyl ester;
(3,5-Di-tert-butyl-4-hydroxy-phenyl)-(3-nitro-benzylamino)-acetic acid ethyl ester;
(3,5-Di-tert-butyl-4-hydroxy-phenyl)-(N-pyrollidinyl)-acetic acid ethyl ester;
(3,5-Di-tert-butyl-4-hydroxy-phenyl)-(N-morpholinyl)-acetic acid ethyl ester;
(3,5-Di-tert-butyl-4-hydroxy-phenyl)-[(N'-methyl)-N-piperazinyl]-acetic acid ethyl ester; and
Diethyl-(3,5-Di-tert-butyl-4-hydroxy-phenyl)-(N-morpholinyl)-acetamide.

13. A method of lowering plasma Lp(a) in a patient, the method comprising administering to a patient in need of Lp(a) lowering a therapeutically effective amount of a compound of claim 1.

14. A method of treating atherosclerosis, the method comprising administering to a patient having atherosclerosis a therapeutically effective amount of a compound of claim 1.

15. A method of treating coronary heart disease, the method comprising administering to a patient having coronary heart disease a therapeutically effective amount of a compound of claim 1.

16. A method of treating or preventing restenosis, the method comprising administering to a patient having restenosis or at risk of having restenosis a therapeutically effective amount of a compound of claim 1.

17. A pharmaceutical composition that comprises a compound of claim 1.

18. A method of lowering plasma Lp(a) in a patient, the method comprising administering to a patient in need of Lp(a) lowering a therapeutically effective amount of a compound of claim 9.

19. A method of treating atherosclerosis, the method comprising administering to a patient having atherosclerosis a therapeutically effective amount of a compound of claim 9.

20. A method of treating coronary heart disease, the method comprising administering to a patient having coronary heart disease a therapeutically effective amount of a compound of claim 9.

21. A method of treating or preventing restenosis, the method comprising administering to a patient having restenosis or at risk of having restenosis a therapeutically effective amount of a compound of claim 9.

22. A pharmaceutical composition that comprises a compound of claim 9.

* * * * *